US012790443B2

(12) United States Patent
Bahuon et al.

(10) Patent No.: US 12,790,443 B2
(45) Date of Patent: Nov. 10, 2026

(54) POLYMERS AND USES THEREOF

(71) Applicant: Hoffmann-La Roche Inc., Little Falls, NJ (US)

(72) Inventors: Floriane Bahuon, Montpellier (FR); Jean Coudane, Montpellier (FR); Vincent Darcos, Paris (FR); Benjamin Nottelet, Montpellier (FR); Sulabh Pravinchandra Patel, Souderton, PA (US); Gregoire Schwach, Basel (CH)

(73) Assignee: Hoffmann-La Roche Inc., Branchburg, NJ (US)

( * ) Notice: Subject to any disclaimer, the term of this patent is extended or adjusted under 35 U.S.C. 154(b) by 385 days.

(21) Appl. No.: 18/208,029

(22) Filed: Jun. 9, 2023

(65) Prior Publication Data

US 2023/0312837 A1 Oct. 5, 2023

Related U.S. Application Data

(63) Continuation of application No. PCT/EP2021/085026, filed on Dec. 9, 2021.

(30) Foreign Application Priority Data

Dec. 11, 2020 (EP) .................................... 20306555
Sep. 29, 2021 (EP) .................................... 21199651

(51) Int. Cl.

| | |
|---|---|
| ***C08G 81/00*** | (2006.01) |
| ***A61K 9/00*** | (2006.01) |
| ***A61K 45/06*** | (2006.01) |
| ***A61K 47/34*** | (2017.01) |

(52) U.S. Cl.

CPC ............ *C08G 81/00* (2013.01); *A61K 9/0051* (2013.01); *A61K 45/06* (2013.01); *A61K 47/34* (2013.01)

(58) Field of Classification Search

CPC ...... C08G 81/00; A61K 9/0051; A61K 45/06; A61K 47/34

See application file for complete search history.

(56) References Cited

U.S. PATENT DOCUMENTS

2020/0069575 A1 3/2020 Liu et al.

FOREIGN PATENT DOCUMENTS

| | | | |
|---|---|---|---|
| CN | 104 558 665 | A | 4/2015 |
| JP | 2019-92532 | A | 6/2019 |
| WO | 2008/019352 | A1 | 2/2008 |
| WO | 2012/009377 | A2 | 1/2012 |
| WO | 2015/035020 | A1 | 3/2015 |
| WO | 2017/137934 | A1 | 8/2017 |
| WO | 2018/191681 | A1 | 10/2018 |

OTHER PUBLICATIONS

Shuqiang Xiong, et al, Poly(e-Caprolactone)-Grafted Polydopamine Particles for Biocomposites with Near-Infrared Light Triggered Self-Healing Ability, 84 Polymer 328 (Year: 2016).*

Cho, J. H. et al., “Bioinspired Catecholic Copolymers for Antifouling Surface Coatings” ACS Appl. Mater. Interfaces 5:3794-3802 (2013).

International Preliminary Report on Patentability—PCT/EP2021/085026 issued Jun. 13, 2023, pp. 1-8.

International Search Report with Written Opinion—PCT/EP2021/085026 mailed Mar. 14, 2022, pp. 1-11.

Liebscher, J., et al., “Structure of Polydopamine: A Never-Ending Story?” Langmuir : the ACS journal of surfaces and colloids 29:10539-10548 (2013).

Liu, X., et al., “Mussel-Inspired Polydopamine: A Biocompatible and Ultrastable Coating for Nanoparticles in Vivo” ACS NANO 7(10):9384-9395 (2013).

Nottelet, B., et al., “Synthesis of an X-ray opaque biodegradable copolyester by chemical modification of poly (ε-caprolactone)” Biomaterials 27:4948-4954 (2006).

Pascolini, D., et al., “Global estimates of visual impairment: 2010” Br J Ophthalmol 96:614-618 (2012).

Pitt, C. G., et al., “A. Aliphatic Polyesters. I. The Degradation of Poly (ϵ-Caprolactone) in Vivo” J. Appl. Polym. Sci. 26:3779-3787 (1981).

Rimpela, A.-K., et al., “Implications of Melanin Binding in Ocular Drug Delivery” Adv. Drug Deliv. Rev. 126:23-43 (2018).

Yasin, M. N., et al., “Implants for Drug Delivery to the Posterior Segment of the Eye: A Focus on Stimuli-Responsive and Tunable Release Systems” JCR 196:208-221 (2014).

* cited by examiner

*Primary Examiner* — Sean M Basquill
(74) *Attorney, Agent, or Firm* — Zong-Qiang Bill Tian

(57) ABSTRACT

Disclosed herein are novel copolymers of poly(ε-caprolactone) (PCL) and polydopamine (PDA), optionally further comprising a PEG chain, methods for making them as well as their use in pharmaceutical preparations, especially implants or in situ gelling depots, for the treatment of ocular disorders or eye diseases.

16 Claims, 28 Drawing Sheets

POLYMERS AND USES THEREOF

CROSS-REFERENCE TO RELATED APPLICATIONS

Figure 1:
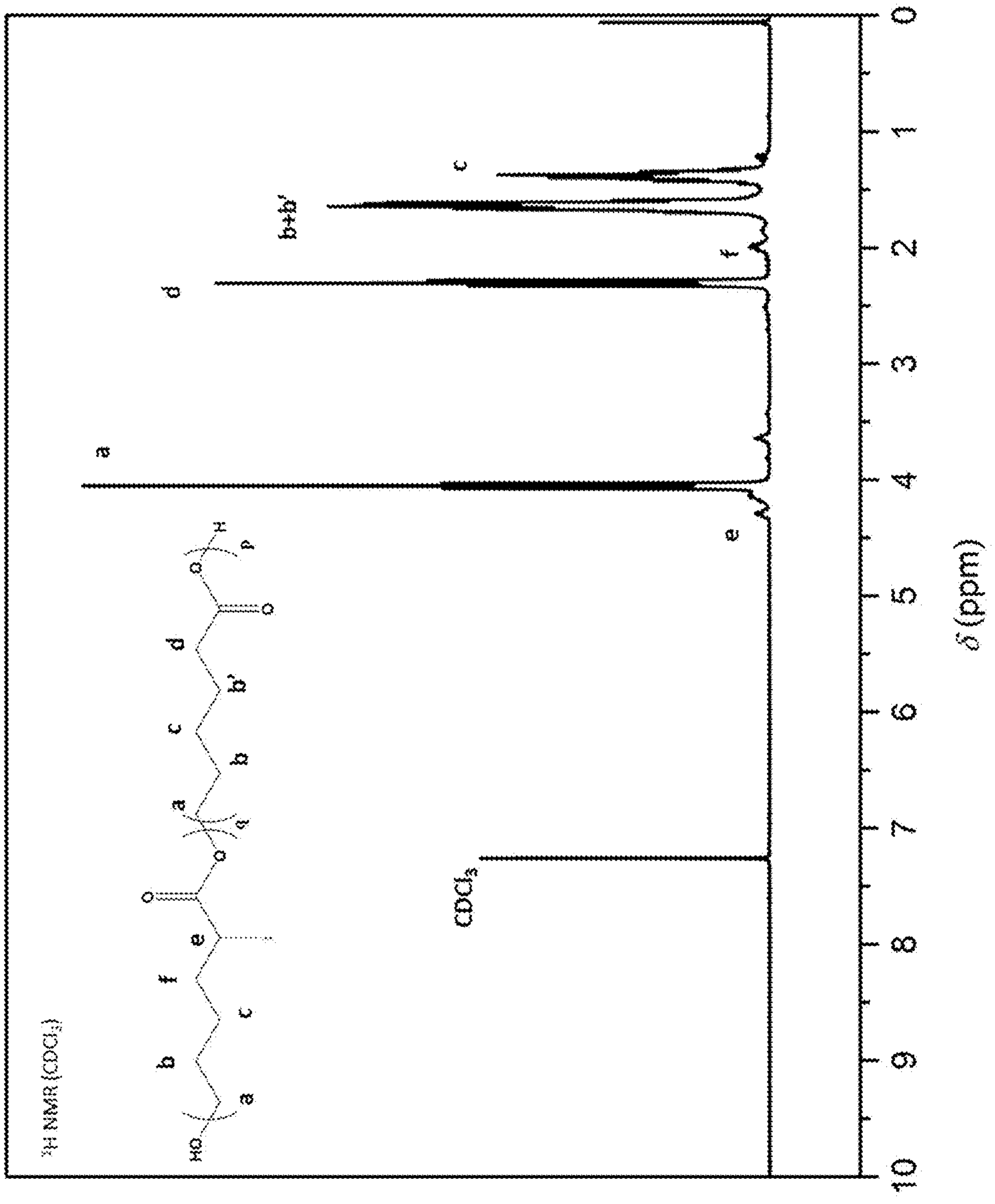

This application is a continuation of International Patent Application No. PCT/EP2021/085026 filed Dec. 9, 2021, which claims the benefit of EP Patent Application No. 20306555.2, filed Dec. 11, 2020 and EP Patent Application No. 21199651.7, filed Sep. 29, 2021 the contents of which are incorporated by reference herein in their entireties. The present invention is generally related to the field of polymers for use as pharmaceutically acceptable carriers, and in particular for the application in the eye.

Around the world, around 39 million people are estimated to be blind, 246 million to be visually impaired. Most of them are people over 50. The main cause of partial and total visual loss come from uncorrected refractive error and cataract, respectively [1]. The main vision posterior segment disorders are the age-related macular degeneration, the diabetic retinopathy and the uveitis. Drugs like corticoids treat these disorders. Some of the drugs are loaded into implantable polymeric devices to be delivered over extended periods of time [2]. In biodegradable polymeric systems, the release of drug is governed by diffusion and polymer degradation. For example, Ozurdex® is the first biodegradable intravitreal implant that was approved by the FDA to treat diabetic macular oedema non-infectious uveitis. Dexamethasone is loaded in poly(lactic acid-co-glycolic acid) (PLGA) matrix based on Novadur® technology. The drug is rapidly released over the two first months then slowly over the four following months. However, PLGA degradation yields to the fragmentation of the implant and to the release of acid moieties that are two possible factors of ocular tissues inflammation. Some non-biodegradable polymers are known in the art such as, for example, Iluvien® intravitreal micro-Implant for 36-mo drug release of fluocinolone acetonide in DME. There remains thus a need to develop novel polymers with improved stability, tolerability and release profile.

SUMMARY OF THE INVENTION

In one embodiment, the present invention provides novel copolymers consisting of poly(ε-caprolactone) (PCL) and polydopamine (PDA).

In one embodiment, the novel copolymer consisting of poly(ε-caprolactone) (PCL) and polydopamine (PDA) is a graft copolymer (PCL-g-PDA).

In one embodiment, the present invention provides methods for making the graft copolymers as disclosed herein.

In another embodiment, the present invention provides the novel PCL-g-PDA copolymers for use in pharmaceutical preparations, in particular as a carrier for sustained release of active ingredients.

In one embodiment, the active ingredient is a small molecule.

In another embodiment, the present invention provides the novel PCL-g-PDA copolymers for use in the treatment of ocular diseases or eye disorders.

In another embodiment, the present invention provides the novel PCL-g-PDA copolymers for use as intravitreal implants.

In another embodiment, the present invention provides the novel PCL-g-PDA, wherein two PCL-g-PDA chains are attached to a PEG chain to form a polymer of the type (PCL-g-PDA)-b-PEG-b-(PCL-g-PDA).

In another embodiment, the present invention provides the polymers of the type (PCL-g-PDA)-b-PEG-b-(PCL-g-PDA), wherein the PEG chain has a molecular weight as defined herein, and the PCL-g-PDA chains both have the same molecular weight.

In another embodiment, the present invention provides the polymers of the type (PCL-g-PDA)-b-PEG-b-(PCL-g-PDA) for use in pharmaceutical preparations, preferably for use in pharmaceutical preparations which form an in situ gelling depot for sustained release of an active pharmaceutical ingredient upon injection in the eye, and wherein said active pharmaceutical ingredient is an antibody.

FIGURES

FIG. 1: $^1$H NMR spectrum in $CDCL_3$ of iodized PCL (PCL-I).

Figure 2:
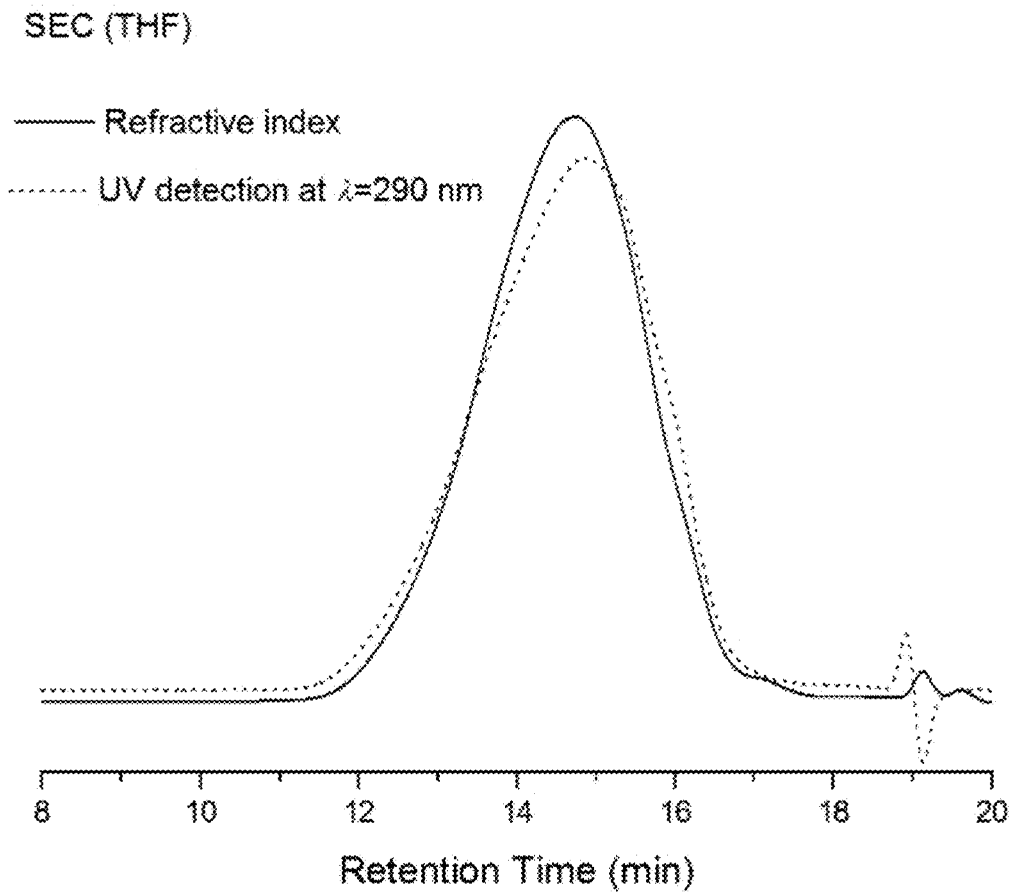

FIG. 2: Size exclusion chromatography in THF of iodized PCL using RI detection and UV detection at λ290 nm.

Figure 3:
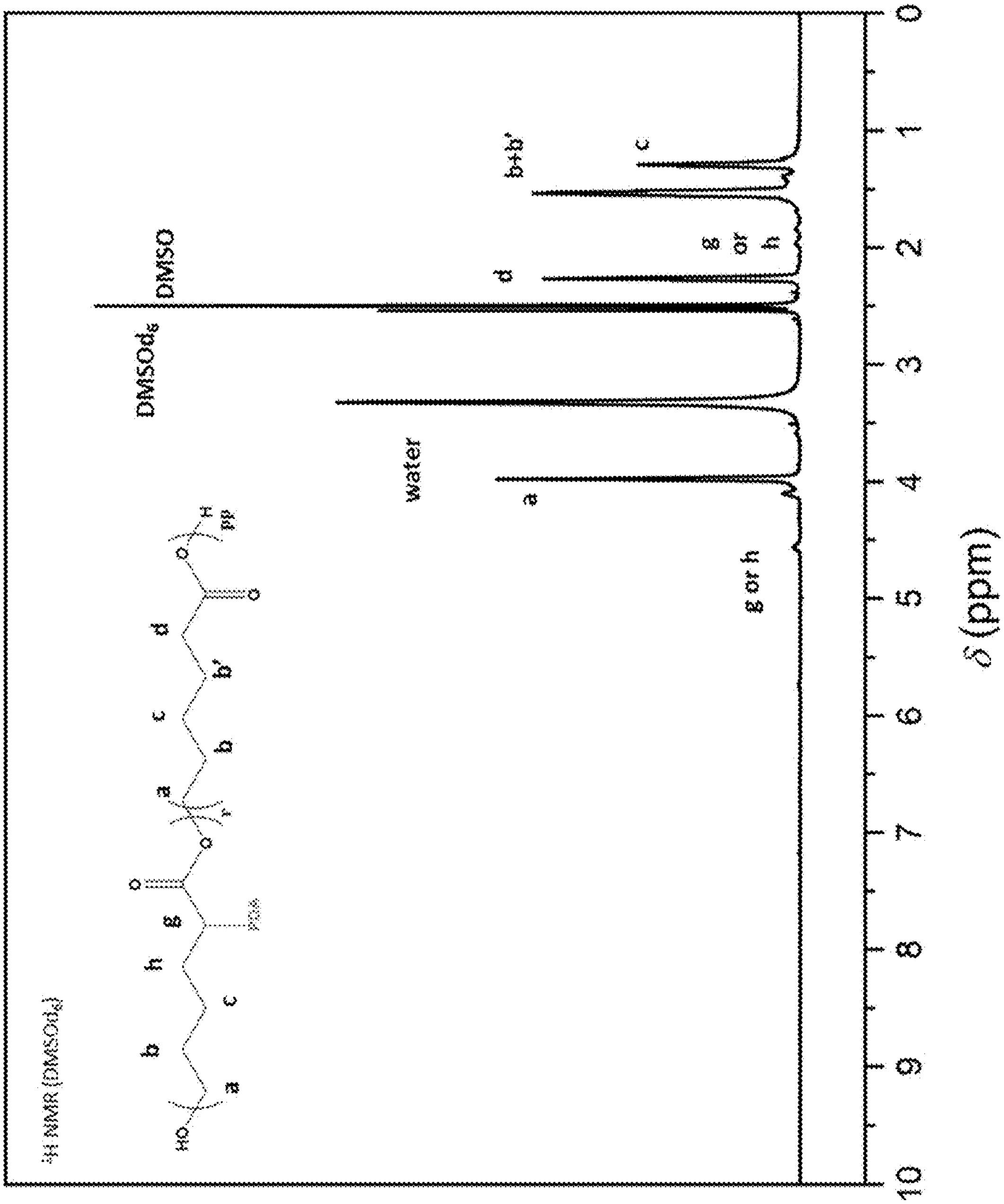

FIG. 3: $^1$H NMR in DMSO-$d_6$ of PCL-g-PDA.

Figure 4:
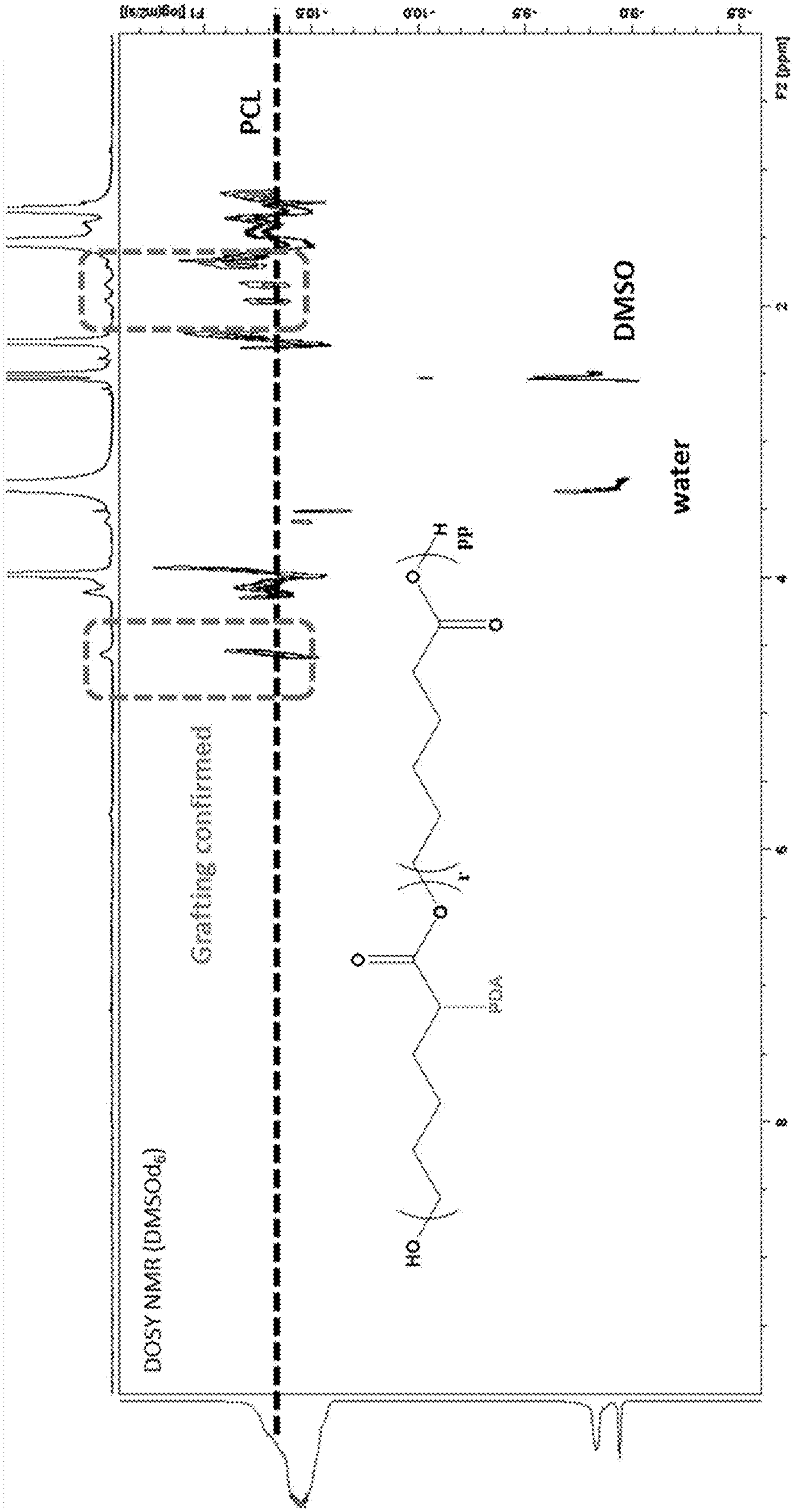

FIG. 4: DOSY NMR in DMSO-$d_6$ of PCL-g-PDA after purification.

Figure 5:
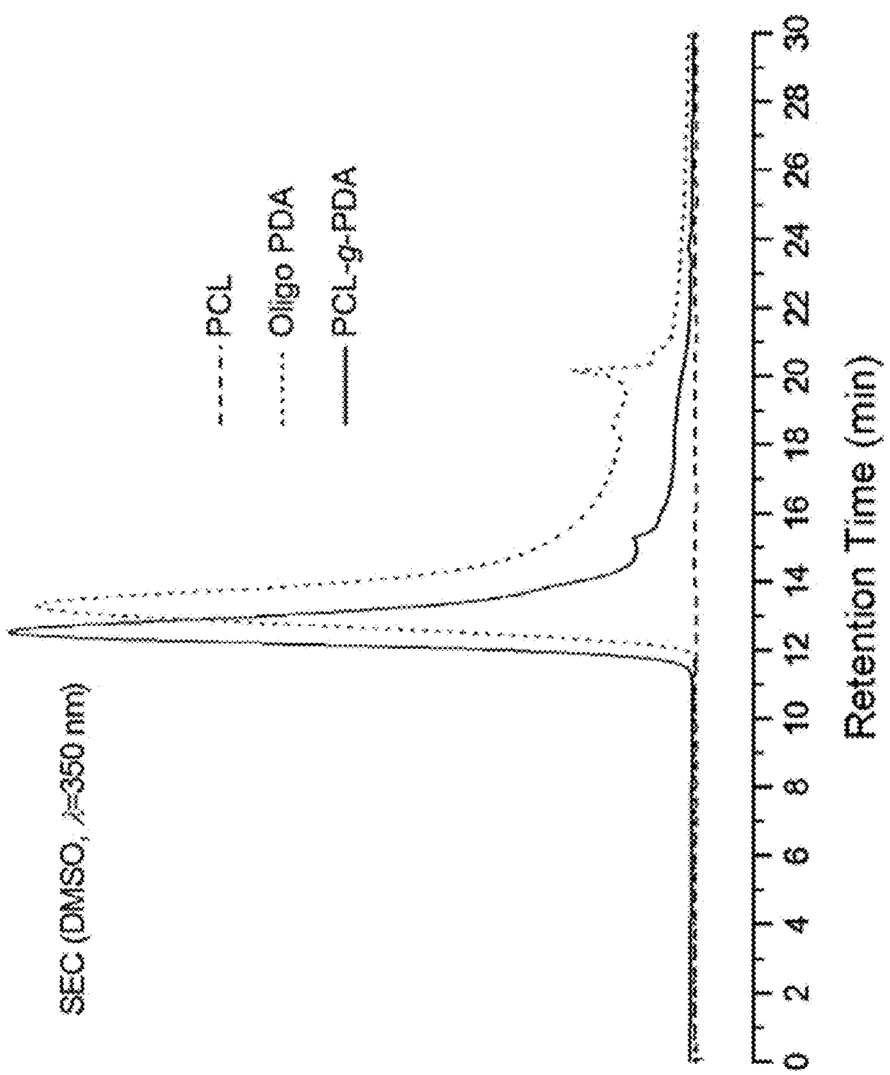

FIG. 5: Size exclusion chromatography in DMSO using UV detection at λ=350 nm of initial commercial PCL, PCL-g-PDA copolymer and oligo PDA.

Figure 6:
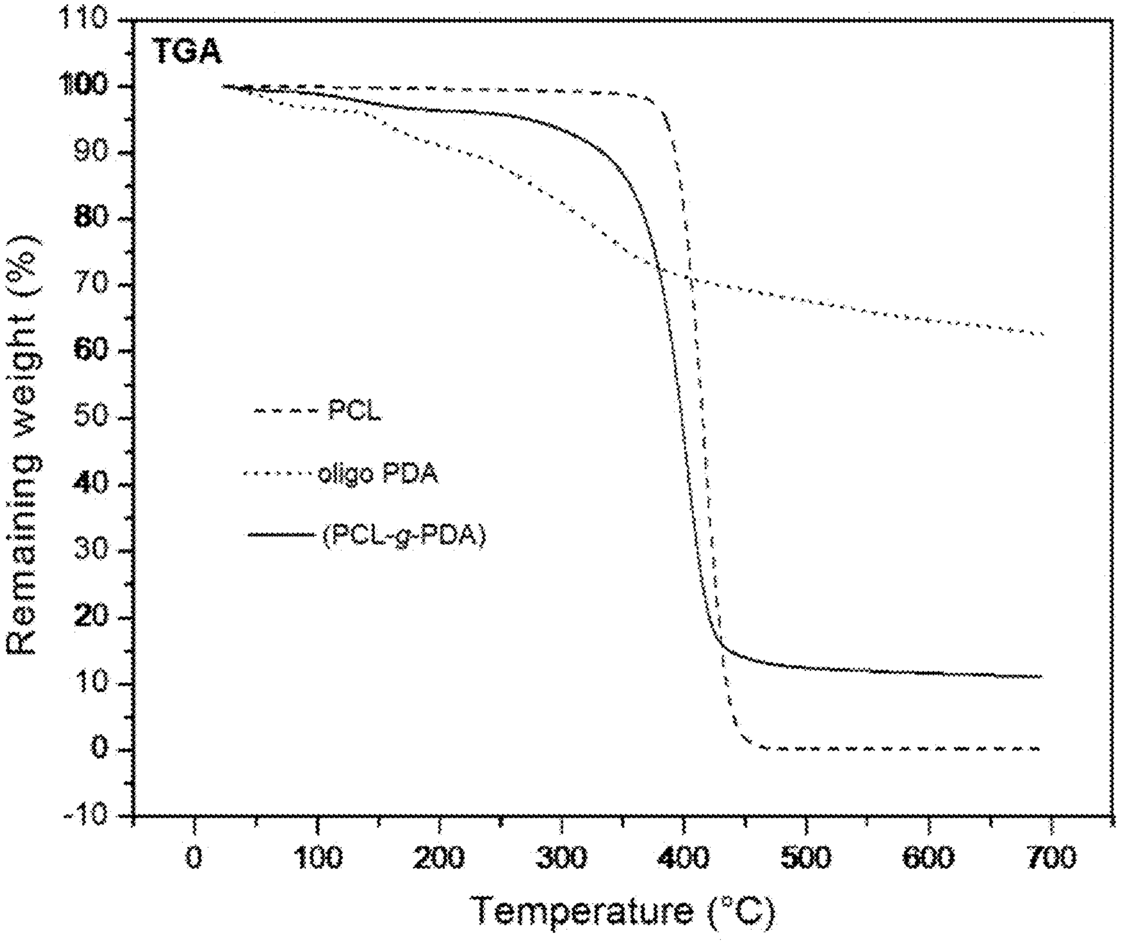

FIG. 6: Thermogravimetric analyses (TGA) of PCL-g-PDA from 30 to 700° C. at 20° C./min under nitrogen atmosphere.

Figure 7:
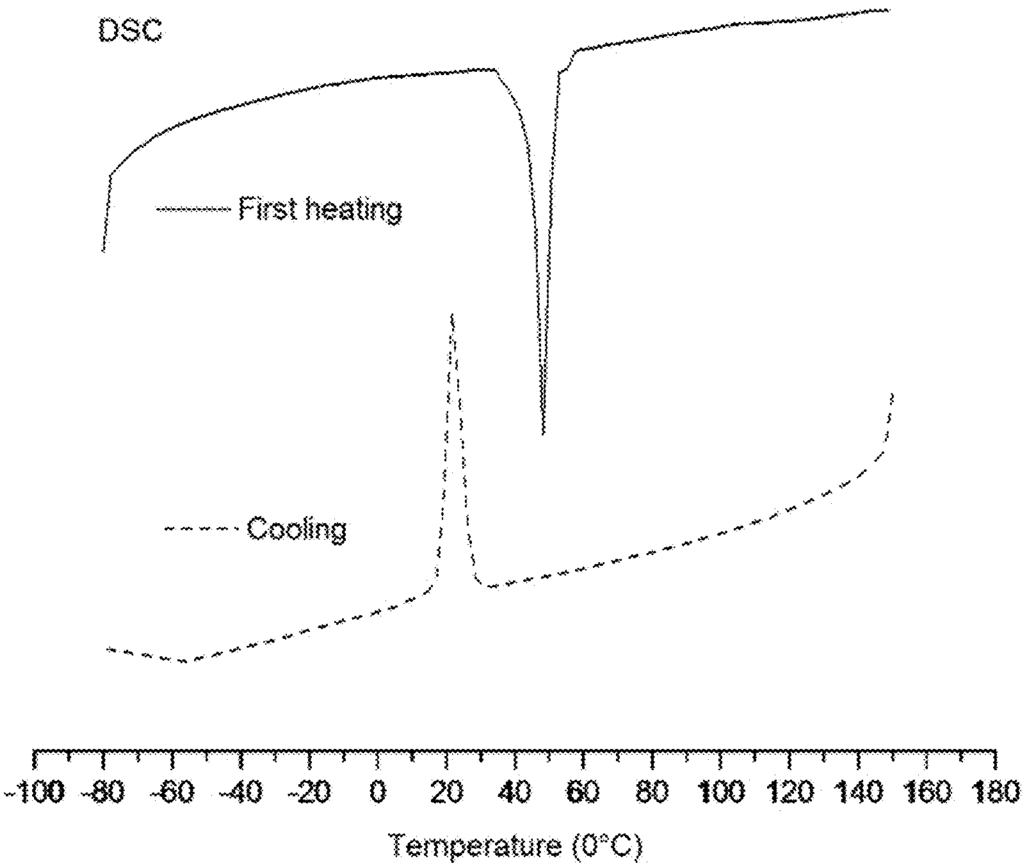

FIG. 7: Differential scanning calorimetry (DSC) thermogram of PCL-g-PDA: first heating ramp from −80 to 150° C. at 10° C./min, cooling ramp from 150 to −80° C. at 10° C./min.

Figure 8:
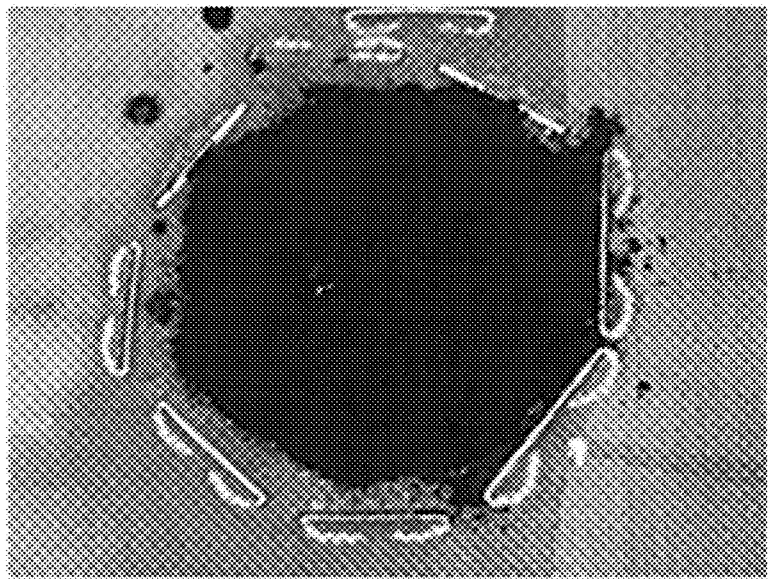

FIG. 8: PCL-g-PDA containing 30 wt. % of DEX prepared by film casting and pressed at 130° C. during 15 mn under 4 tons (One staple equals 1.2 cm, the thickness of the film is about 500 μm).

Figure 9A:
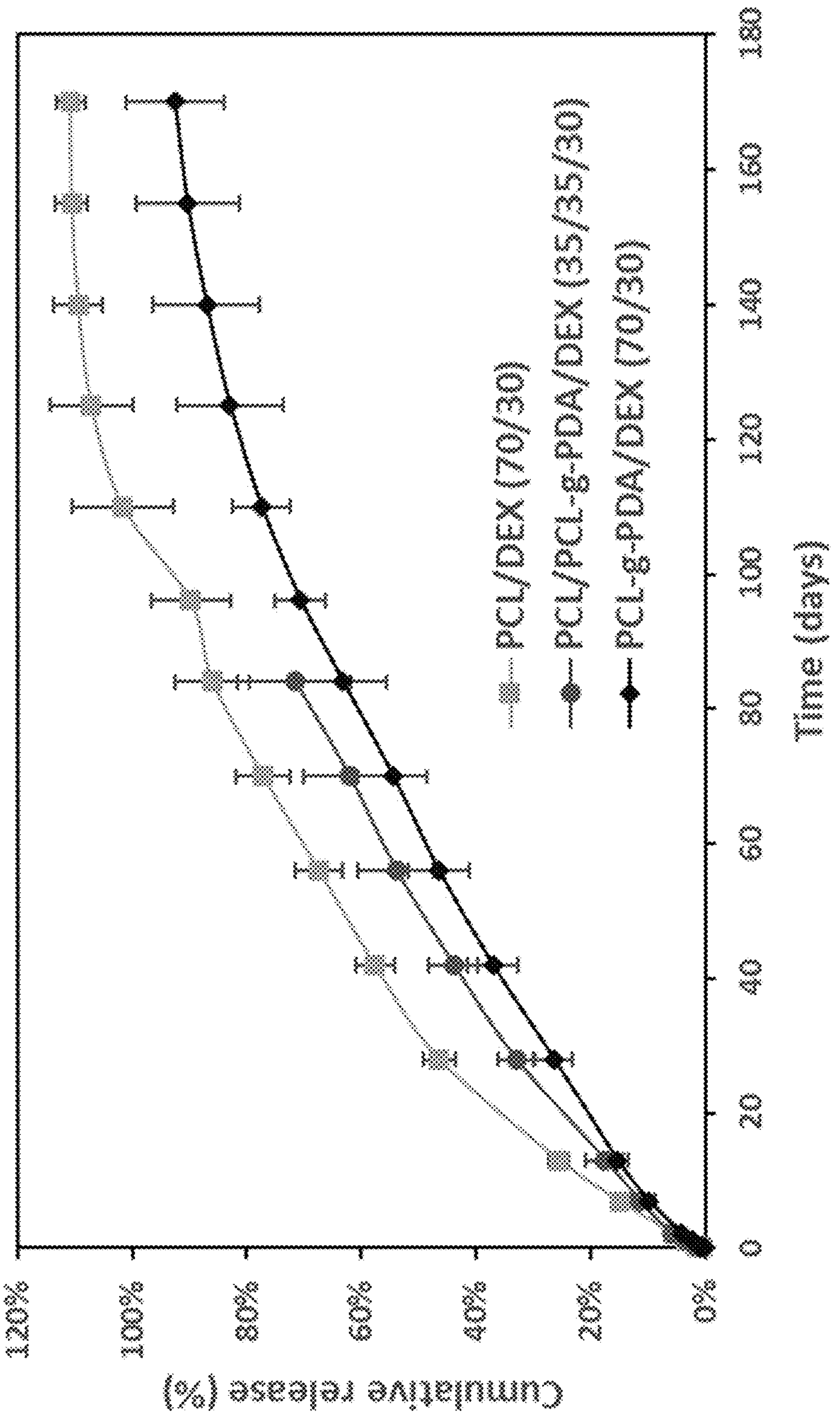
Figure 9B:
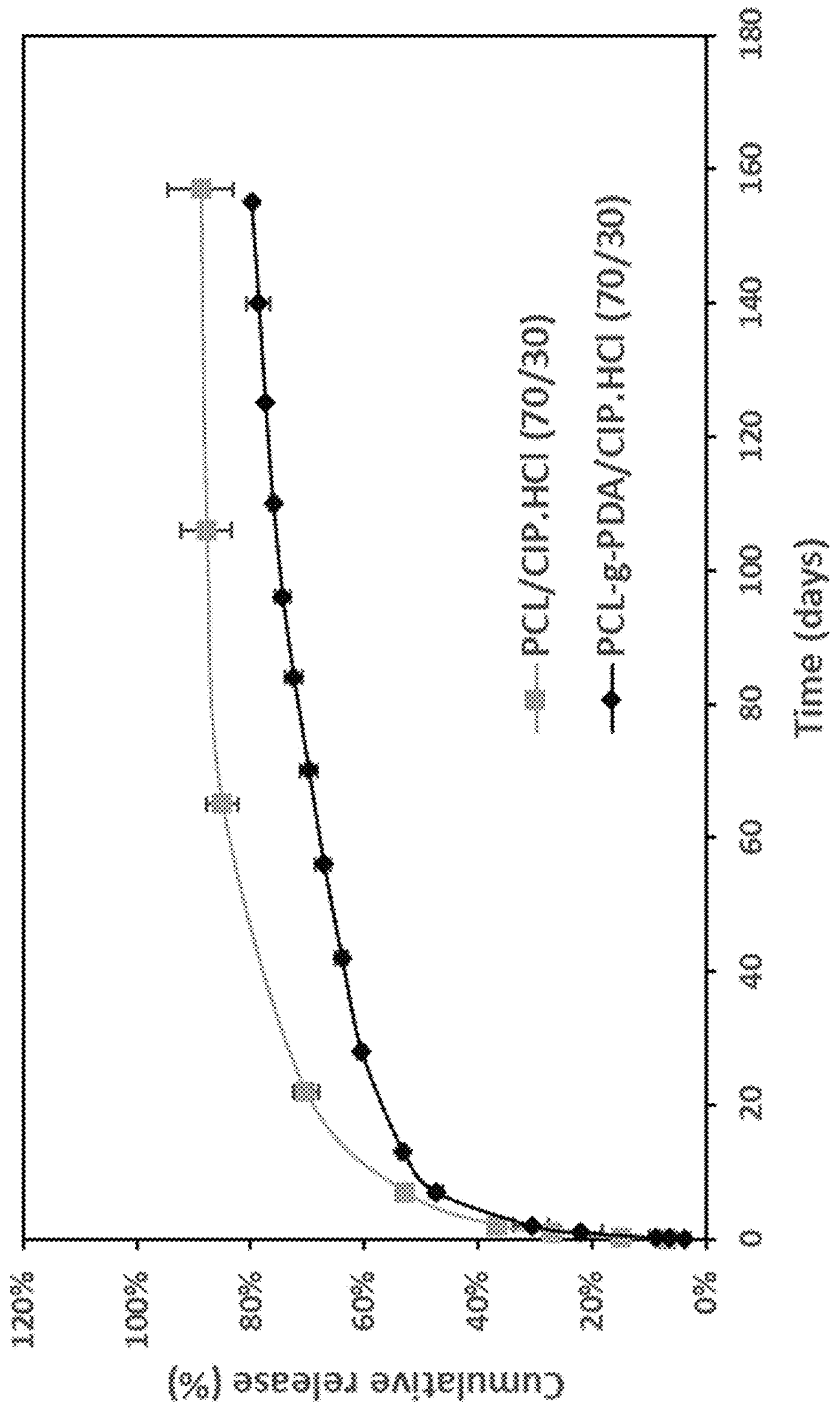

FIG. 9A and FIG. 9B: Cumulative release of (FIG. 9A) dexamethasone (DEX30) and (FIG. 9B) ciprofloxacin hydrochloride (CIP30) from PCL and PCL-g-PDA implants as a function of implant composition. Data are expressed selection as an average of results obtained from measurements by HPCL (mean±SD; n=3). PDA content is estimated at 5 wt. % by TGA.

Figure 10:
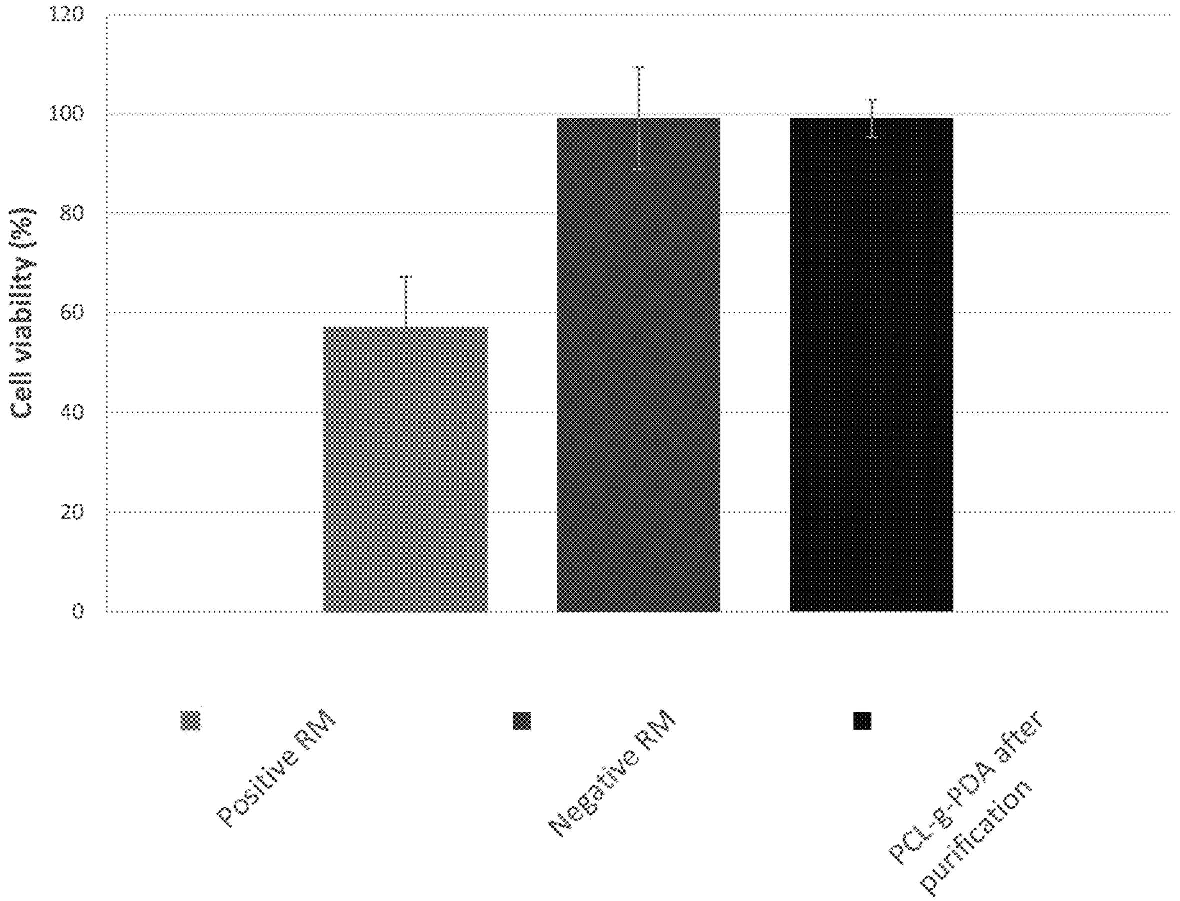

FIG. 10: Viability of L929 cells after 24 h incubation with PCL-g-PDA film. Percentages obtained from the fluorescence intensities after PrestoBlue test.

Figure 11:
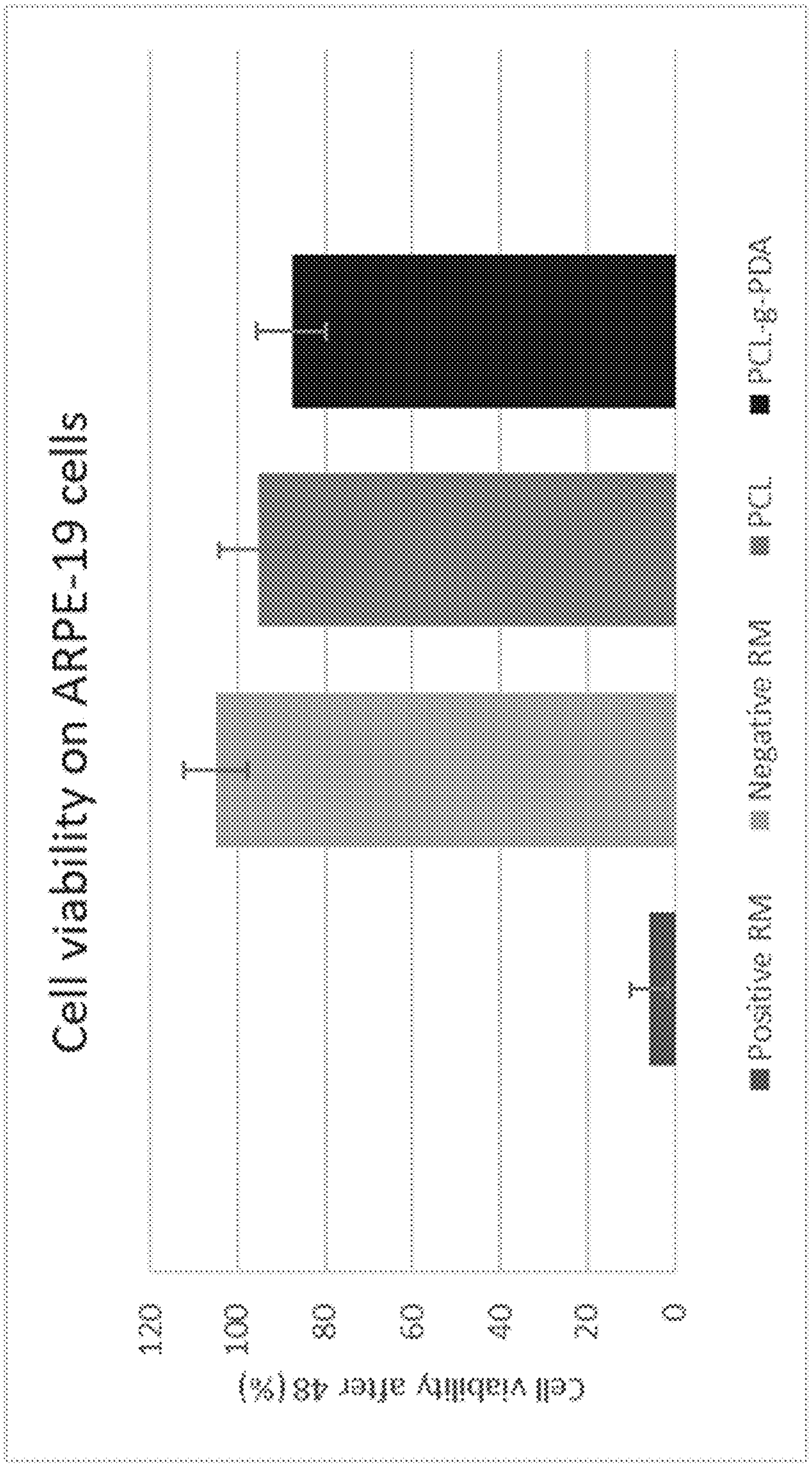

FIG. 11: Viability of ARPE-19 (ATCC, CRL-2302), human retinal epithelial cell line after 48 h of incubation with PCL or PCL-g-PDA film.

Figure 12:
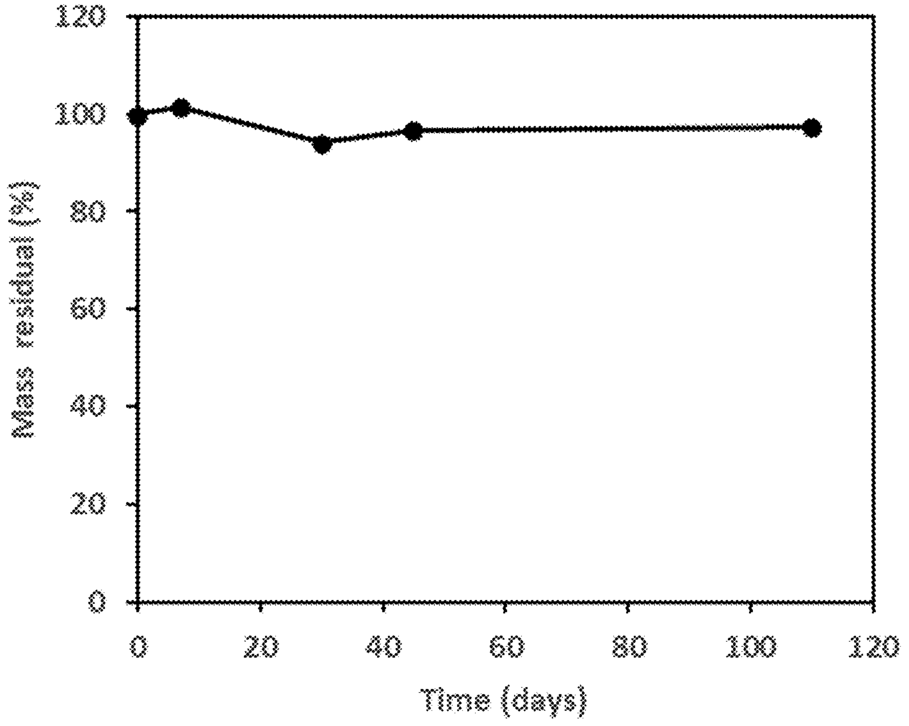

FIG. 12: Residual mass of PCL-g-PDA during degradation study in standard conditions (PBS, 37° C., pH=7.4)

Figure 13:
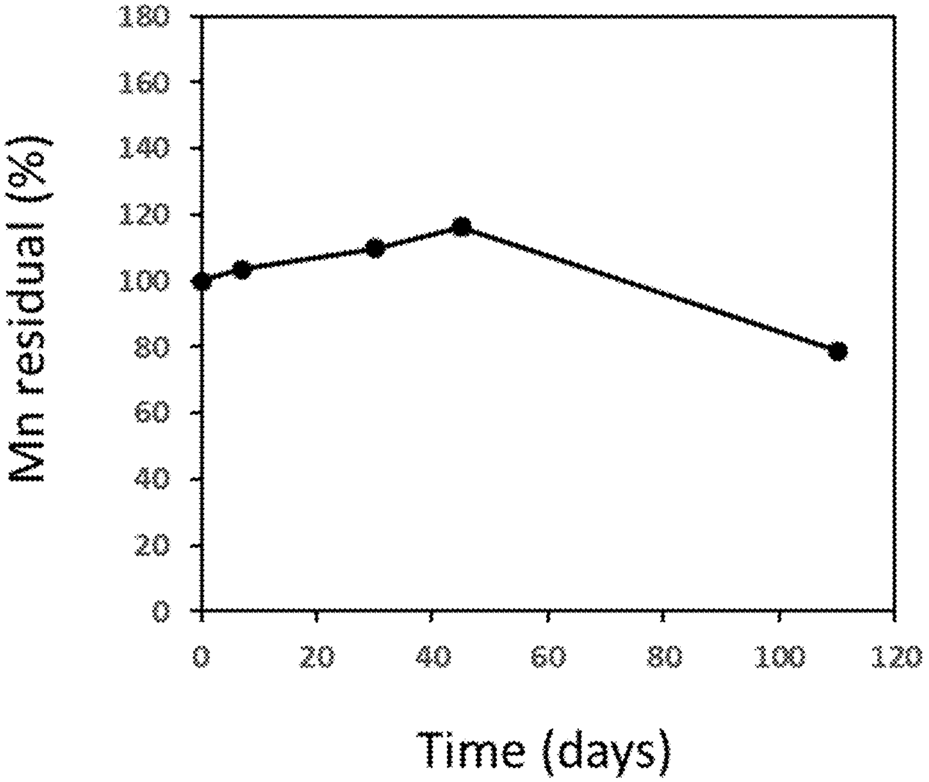

FIG. 13: Residual molecular weight of PCL-g-PDA during degradation study in standard conditions (PBS, 37° C., pH=7.4)

Figure 14:
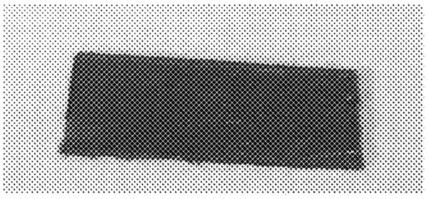

FIG. 14: Photograph of the PCL-g-PDA implant after 110 days of immersion in standard conditions (PBS, 37° C., pH=7.4)

Figure 15:
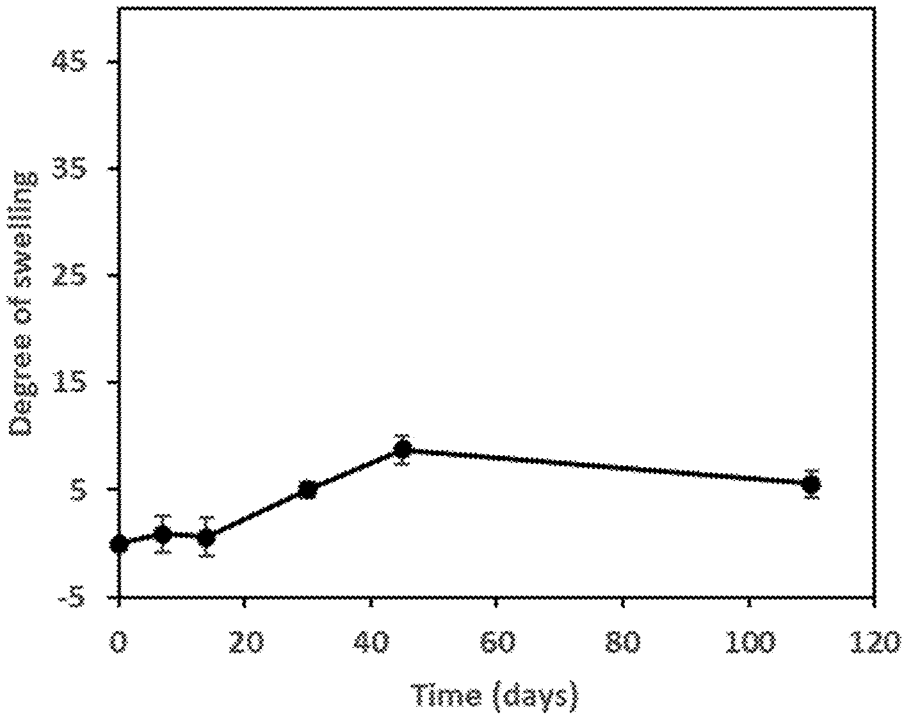

FIG. 15: Degree of swelling of PCL-g-PDA during degradation study in standard conditions (PBS, 37° C., pH=7.4)

Figure 16:
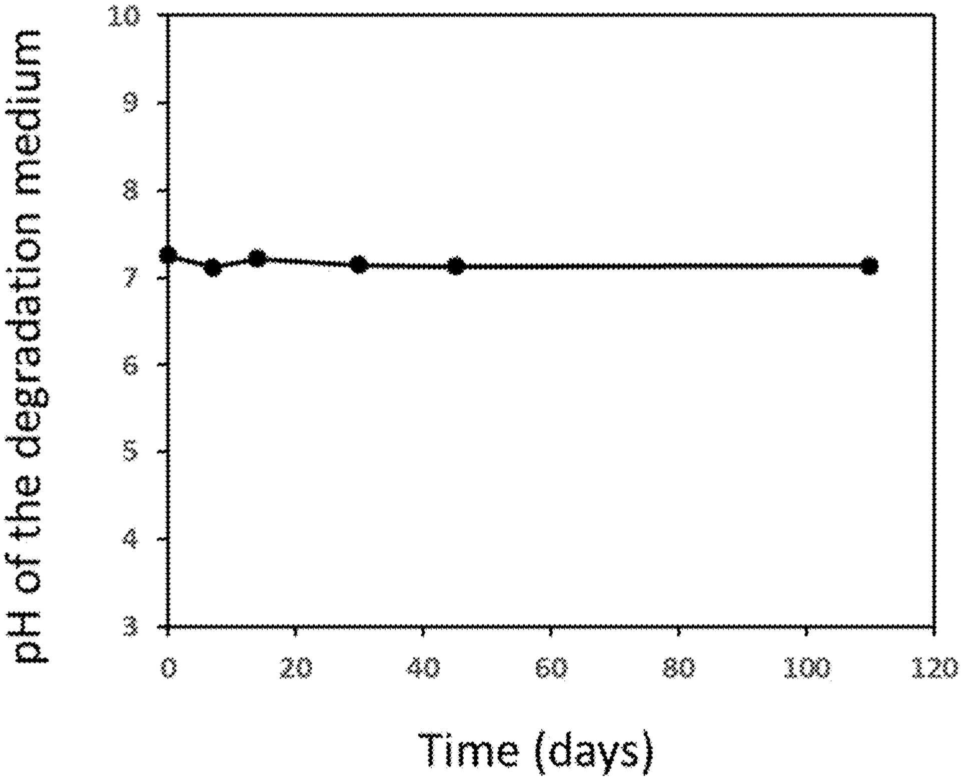

FIG. 16: pH of the degradation medium during degradation study of PCL-g-PDA implant in standard conditions (PBS, 37° C., pH=7.4)

Figure 17:
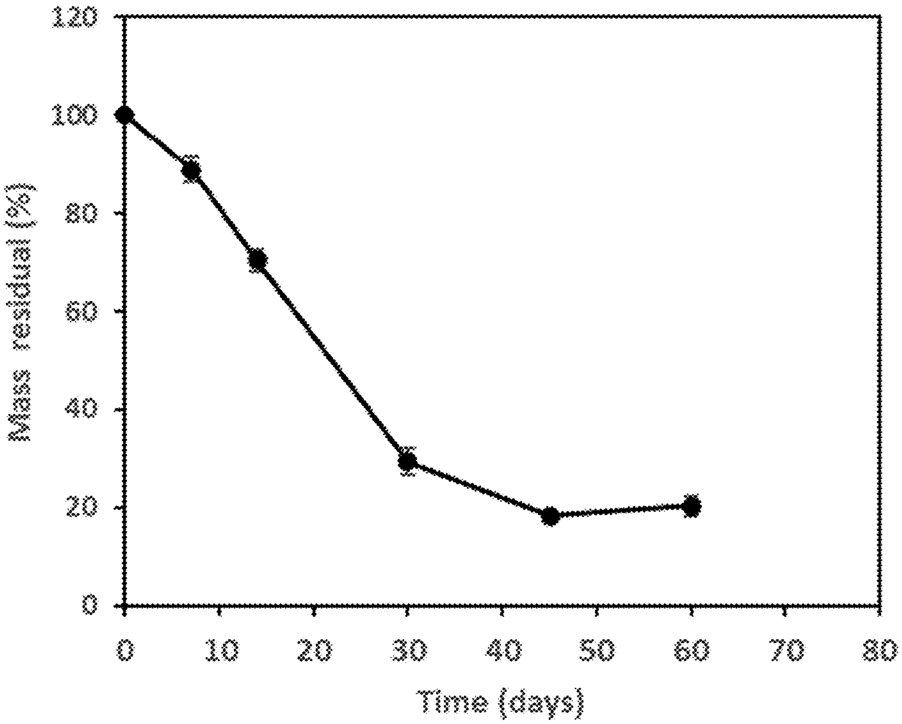

FIG. 17: Residual mass of PCL-g-PDA during degradation study in accelerated conditions (HCl (2M), 37° C., pH=1)

Figure 18:
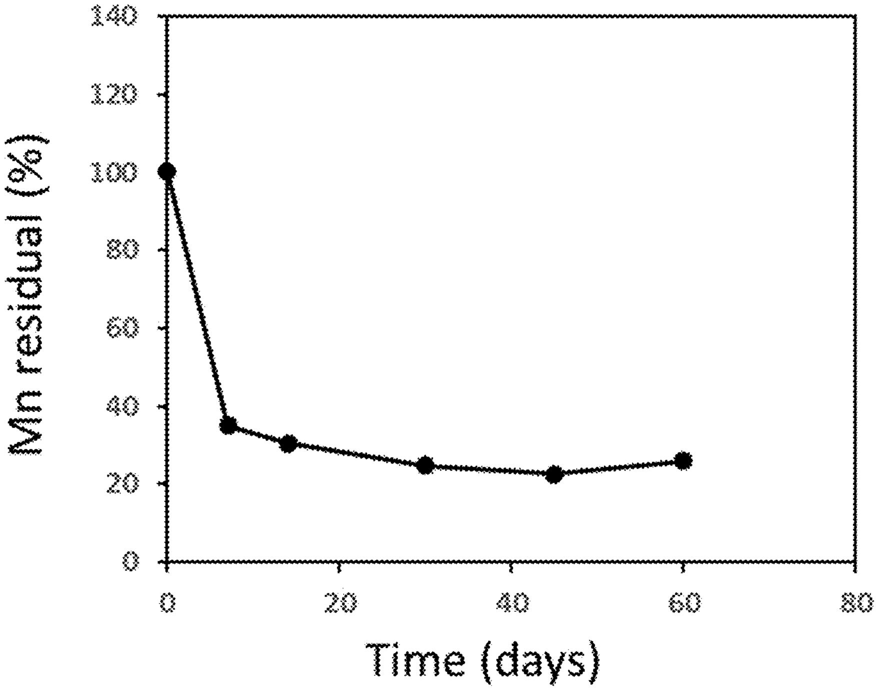

FIG. 18: Residual molecular weight of PCL-g-PDA during degradation study in accelerated conditions (HCl (2M), 37° C., pH=1)

Figure 19:
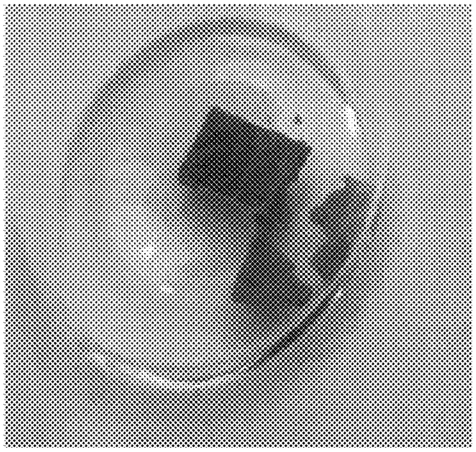

FIG. 19: Photograph of the PCL-g-PDA implant after 60 days of immersion in accelerated conditions (HCl (2M), 37° C., pH=1)

Figure 20:
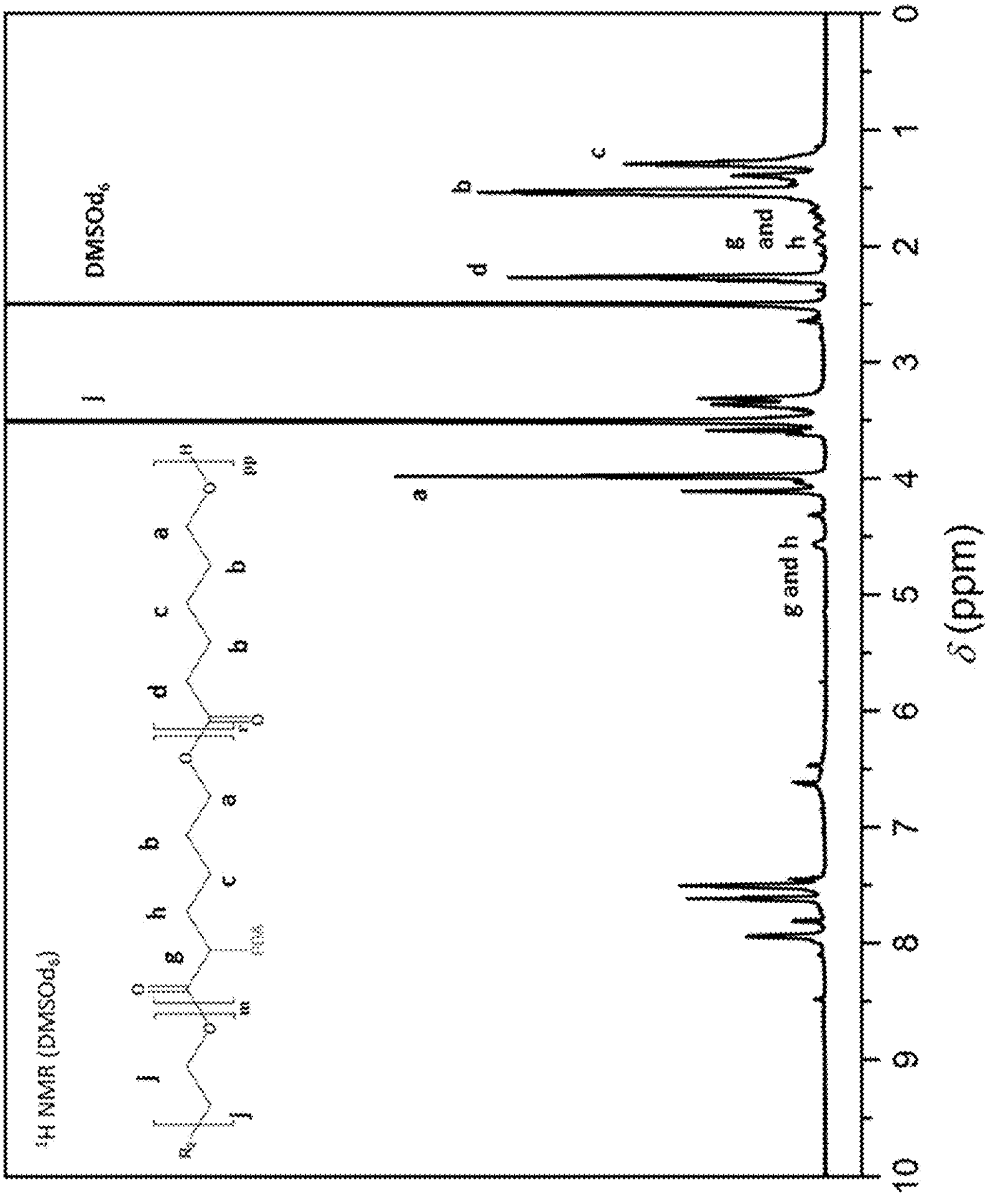

FIG. 20: $^{1}H$ NMR in DMSO-$d_6$ of T-PDA.

Figure 21:
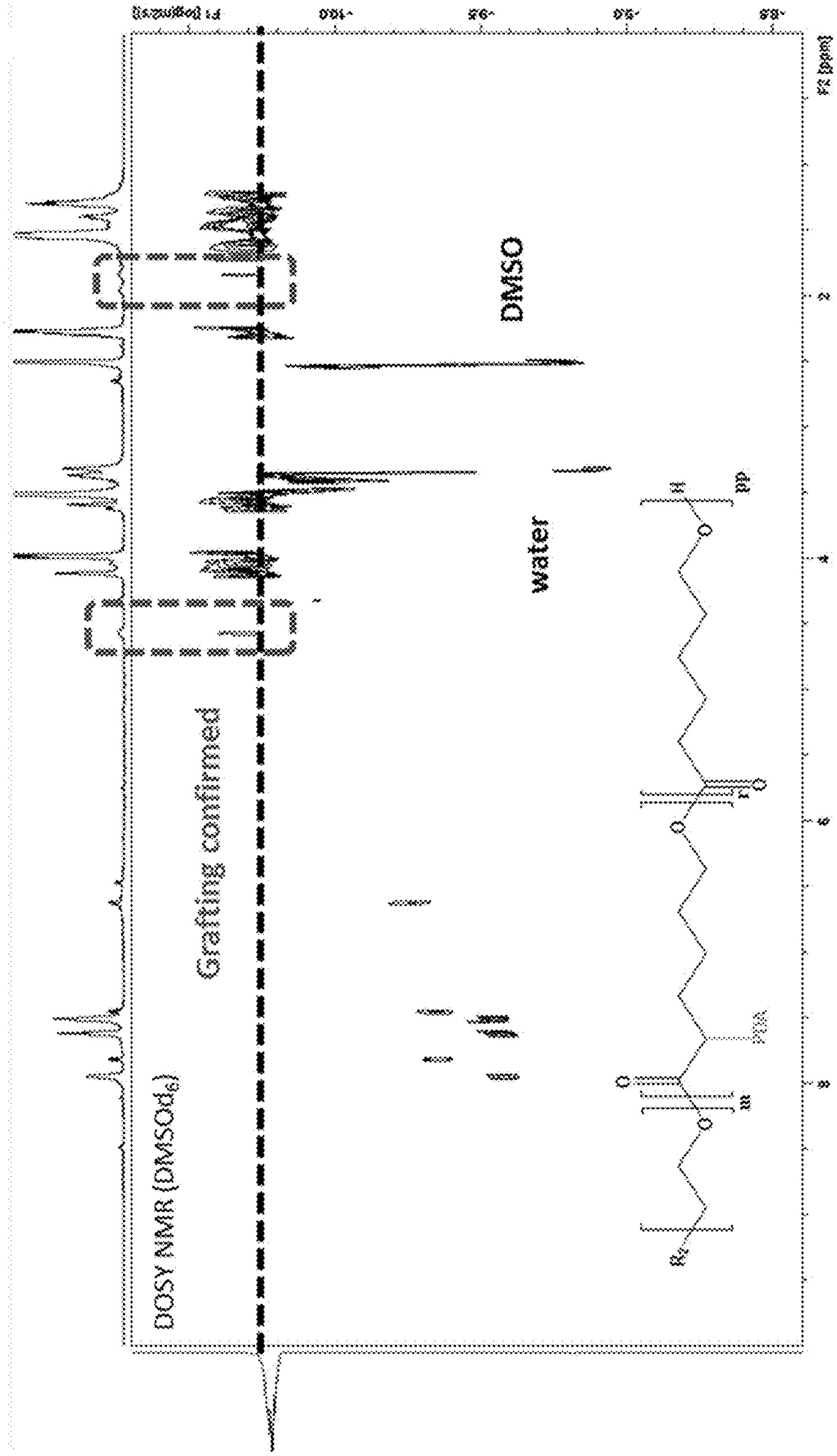

FIG. 21: DOSY NMR in DMSO-$d_6$ of T-PDA

Figure 22A:
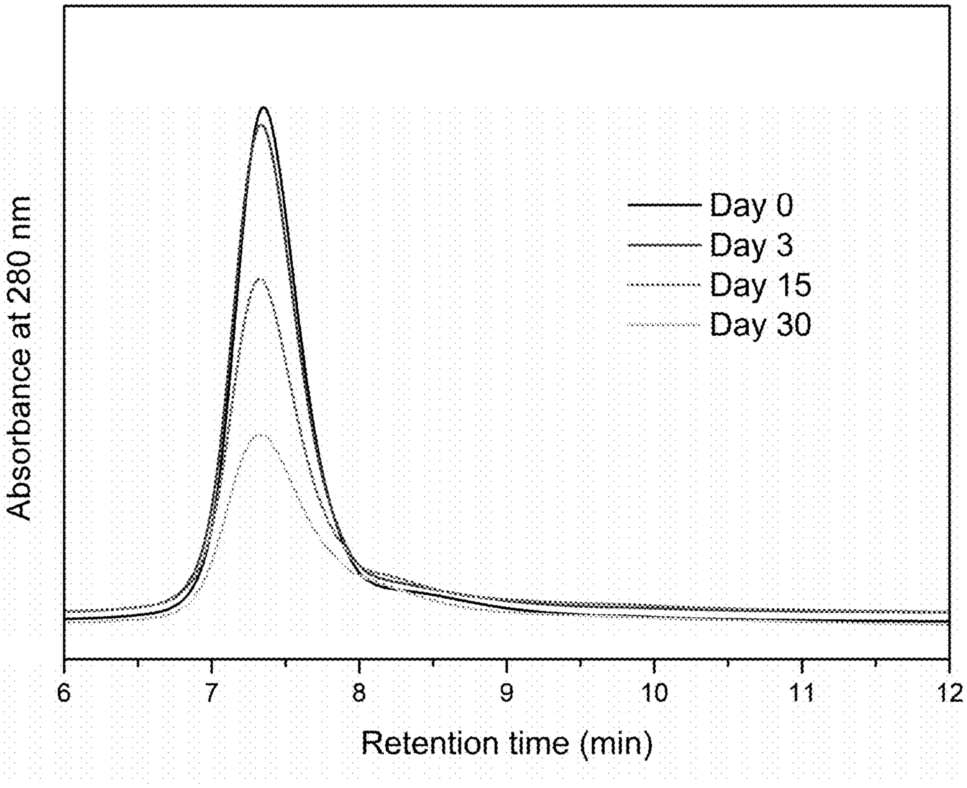
Figure 22B:
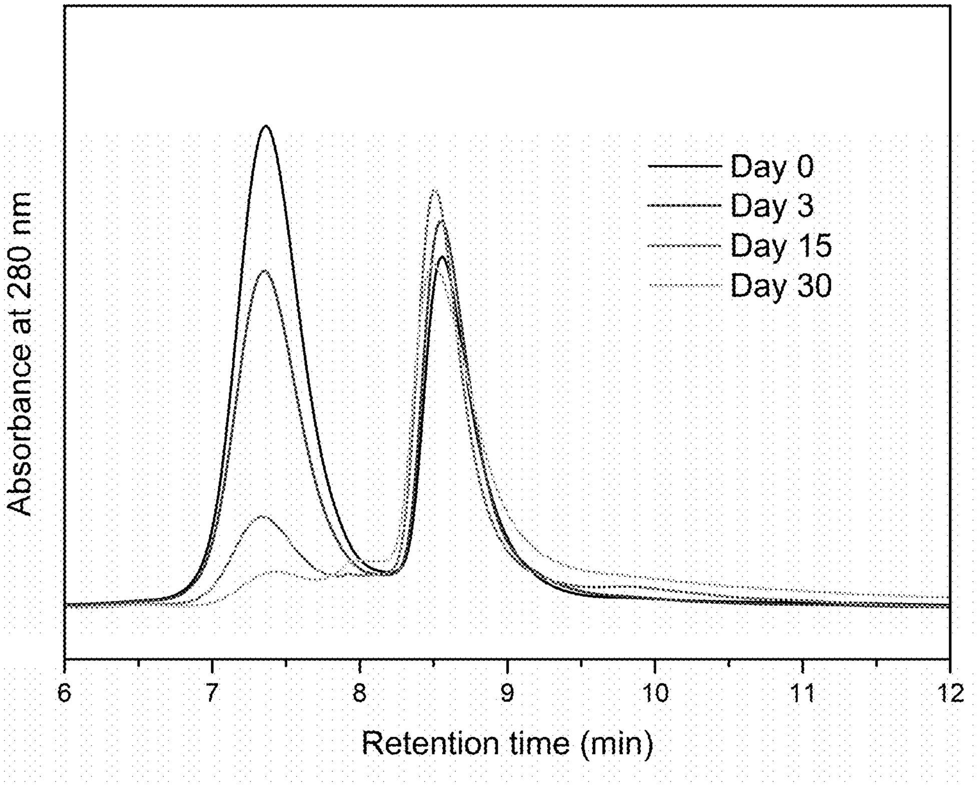
Figure 22C:
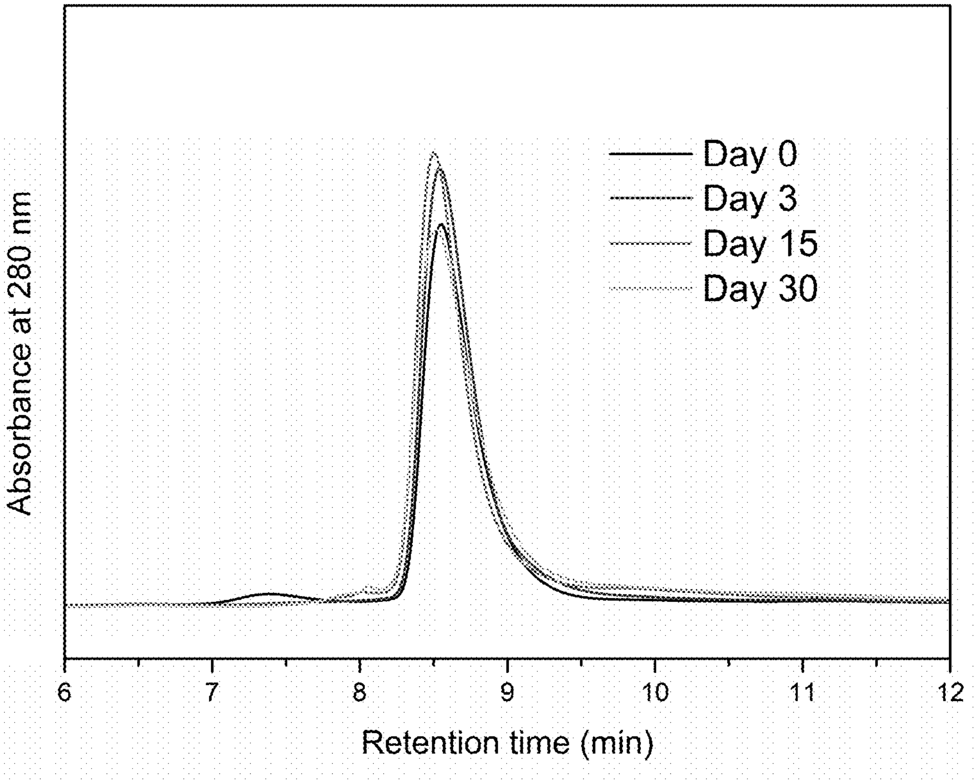

FIG. 22A, FIG. 22B and FIG. 22C: Size exclusion chromatography at 280 nm during stability study of mAb in formulations composed of (FIG. 22A) T-HD, (FIG. 22B) T/T-PDA-HD (2:1), and (FIG. 22C) T-PDA-HD in HBS: PEG400=1:1.

Figure 23A:
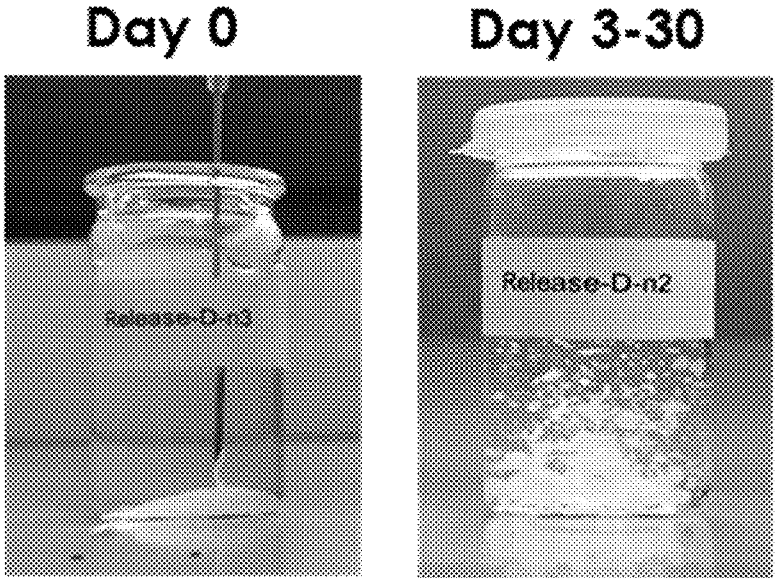
Figure 23B:
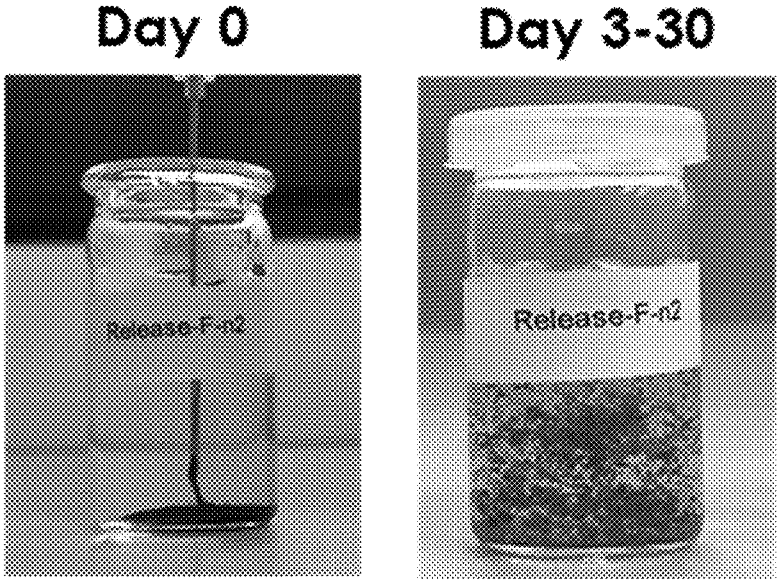
Figure 23C:
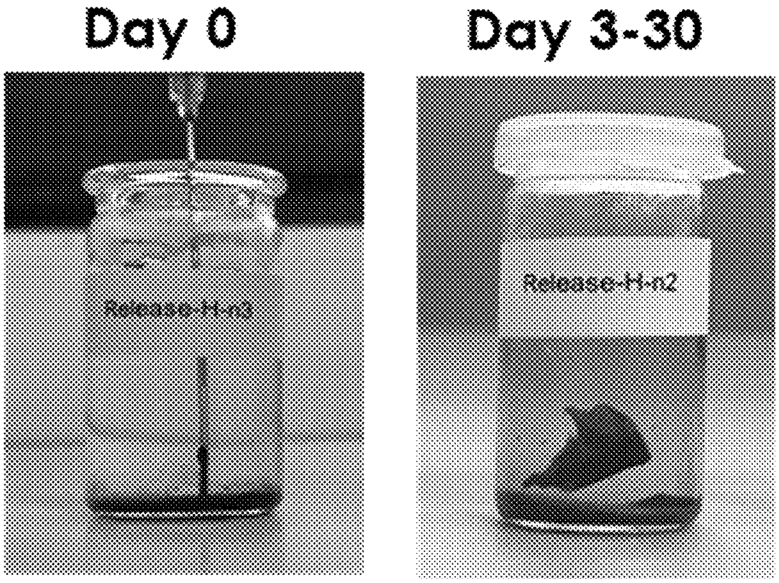

FIG. 23A, FIG. 23B and FIG. 23C: The formation and the evolution of the aspect during 30 days of the in-situ depots for the formulations (FIG. 23A) T-HD, or (FIG. 23B) T/T-PDA-HD (2:1) and (FIG. 23C) T-PDA-HD.

DETAILED DESCRIPTION OF THE INVENTION

Most ocular diseases are conditions or disorders that interfere with the ability of the eye to function properly and/or that negatively affects the visual clarity and are a major public health issue. The intravitreal (IVT) administration—including implantation of medical devices or injection of suspensions, solutions or implant—is a routine method and is the most efficient one to deliver APIs to the retina. The main challenges of the IVT administration are the decrease in the frequency of injection to improve the patient compliance and adherence to the treatment, the ocular tolerability of the formulations and the stability of the biologics. At present, it is still challenging to satisfy all the specifications and the formulations based on polymer technology are marginal, recent but may solve those issues. Scientists are focusing their efforts on developing biocompatible, (bio)degradable or not, formulations providing long and sustained delivery of APIs with a minimal surgery operation in order to increase the well-being of patients and to reach therapeutic level to treat efficiently the ocular diseases.

The objective of the present invention is to evaluate the benefits of incorporation of PDA units in the design of novel copolymers for ophthalmology, with improved tolerability and superior sustained release features (of small or large molecules) thanks to preferential drug-PDA interactions. Among the polymers used in medical and/or drug delivery applications, the degradable synthetic-based formulations show interesting and promising properties. Particularly, PCL is biodegradable, degrades slowly, can be functionalized and is approved by the FDA for medical purpose (but not ophthalmic yet). Also, PEG is bio eliminable (function of its molecular weight), approved by the FDA for ophthalmic application and offer tunable gelation properties in combination with PCL.

The present inventors developed two strategies, one solid formulation for the delivery of small molecules (Chapter I), and the other one, an in situ gelling system for the delivery of biologics (Chapter II).

Chapter I: PCL-g-PDA Solid Implants

The solid implant approach provides a hydrophobic grafted copolymer PCL-g-PDA. The copolymer was synthesized in a two-step process. Firstly, the PCL (Mn=190 000 g/mol) was post-functionalized by iodine via an electrophilic substitution to give an iodinated PCL (PCL-I). Secondly, PCL-I was functionalized by PDA under ATRP-like, oxidative and basic conditions to give a PCL-g-PDA copolymer containing about 3-5 wt. % of grafted PDA. The in vitro cytotoxicity assays showed that the implants PCL-g-PDA were non-cytotoxic on mouse fibroblast cells and retinal cells. Besides, the implants were not degraded in physiological conditions over 110 days but degraded under accelerated conditions, proving the ability of PCL-g-PDA implant to degrade slowly. In vitro, PCL-g-PDA implants showed a sustained, constant and complete release (zero-order kinetics) of water-insoluble dexamethasone (DL=30% w/w) during 155 days. In contrast PCL-g-PDA implants showed a burst effect followed by a sustained release of water-soluble ciprofloxacin hydrochloride (DL=30% w/w) during 125 days with an extrapolation of complete release after around 500 days. In all cases, the kinetics of release for PCL-g-PDA implants were slower compared with PCL implants, thus showing the ability of PDA to retain the drug inside the implant, even with a low amount of grafted PDA. Moreover, PCL and PCL-g-PDA implants showed a longer release time of dexamethasone compared to the commercial PLGA-based implant (Ozurdex™).

Therefore, in accordance with the present invention there are provided new intravitreal implants that can provide a sustained-drug delivery over several months and that have a slow degradation to avoid changing the micro-environmental media and avoid fragmentation. In one embodiment said sustained drug delivery is provided for at least 2 months, or for at least 3 months, or for at least 6 months, or for at least 12 months, or for at least 18 months, or for at least 24 months, or for at least 36 months. The implant is made of poly(ε-caprolactone) (PCL) and polydopamine [3] (PDA). PCL is a biocompatible hydrophobic and FDA-approved polymer. It degrades slowly by hydrolysis covering extended and larger period of release. Melanin is located into retinal cells and participated to biological functions [4]. PDA is a biocompatible [5] synthetic melanin-like polymer exhibiting possibly the same properties than melanin, especially drug-binding properties. The present inventors have found that combining both polymers leads to improved biocompatibility or tolerability, and sustained release with limited micro-environmental change.

Therefore, in one embodiment, the present invention provides novel copolymers consisting of poly(ε-caprolactone) (PCL) and polydopamine (PDA). In another embodiment, the novel copolymer consisting of poly(ε-caprolactone) (PCL) and polydopamine (PDA) is a graft copolymer (PCL-g-PDA).

The term PCL as used herein means poly(ε-caprolactone). In one embodiment, PCL has a molecular weight in the range of 1000 g/mol to 200 000 g/mol. In another embodiment, PCL has a molecular weight in the range of 10 000 g/mol to 100 000 g/mol.

The term PDA as used herein means polydopamine.

The term graft-copolymer (or graft-polymer) means segmented copolymers with a backbone, linear or branched, of one composite (e.g. PCL) and randomly distributed branches of another composite (e.g. PDA). In one embodiment, the PCL backbone is linear.

In one embodiment, the PCL-g-PDA copolymers according to the present invention comprise PCL of a molecular weight in the range of 1000 g/mol to 200 000 g/mol; or 10 000 g/mol to 100 000 g/mol.

Prior to polymerization reaction with PDA, PCL is chemically modified, for example by electrophilic substitution, to yield halogenated, for example, iodized PCL [6]. Therefore, in one embodiment the copolymers according to the present invention are obtained using halogenated PCLs with molecular weight in the range of 1000 g/mol to 100 000 g/mol; or 2500 g/mol to 50 000 g/mol, and with molar percentage of iodized ε-caprolactone units in the range 0.1 to 50 mol. %; or 1 to 20 mol. %. The term "halogenated" has the ordinary meaning known to a person of skill in the art. In one aspect, the PCLs are brominated, chlorinated or iodized.

In another embodiment the present PDA-g-PCL has a PDA mass content in the range of 0.1 to 50 wt. %, or 1 to 20 wt. %, or 1 to 15 wt. %, or 1 to 10 wt. %, or about 5 wt. % PDA.

The term wt. % (or weight %) has its ordinary meaning to a person of skill in polymer chemistry. Preferably wt. % means a mass relative to the total mass of the graft copolymer. Unless explicitly stated otherwise, the wt. % for the PDA content in the present graft copolymers is calculated after purification and measured by TG analysis, as for example described herein.

In another embodiment, the graft copolymer according to the present invention consists of a PCL backbone with a molecular weight of 1000 g/mol to 200 000 g/mol and random branches of PDA with a mass content of 0.1 to 50 wt. %.

In another embodiment, the graft copolymer according to the present invention consists of a PCL backbone with a molecular weight of 1000 g/mol to 200 000 g/mol and random branches of PDA with a mass content of 1 to 20 wt. %.

In another embodiment, the graft copolymer according to the present invention consists of a PCL backbone with a molecular weight of 1000 g/mol to 200 000 g/mol and random branches of PDA with a mass content of 1 to 10 wt. %.

In another embodiment, the graft copolymer according to the present invention consists of a PCL backbone with a molecular weight of 1000 g/mol to 200 000 g/mol and random branches of PDA with a mass content of about 5 wt. %.

In another embodiment, the graft copolymer according to the present invention consists of a PCL backbone with a molecular weight of 10 000 g/mol to 100 000 g/mol and random branches of PDA with a mass content of 0.1 to 50 wt. %.

In another embodiment, the graft copolymer according to the present invention consists of a PCL backbone with a molecular weight of 10 000 g/mol to 100 000 g/mol and random branches of PDA with a mass content of 1 to 20 wt. %.

In another embodiment, the graft copolymer according to the present invention consists of a PCL backbone with a molecular weight of 10 000 g/mol to 100 000 g/mol and random branches of PDA with a mass content of 1 to 10 wt. %.

In another embodiment, the graft copolymer according to the present invention consists of a PCL backbone with a molecular weight of 10 000 g/mol to 100 000 g/mol and random branches of PDA with a mass content of about 5 wt. %.

In another embodiment, the graft copolymer according to the present invention consists of a PCL backbone with a molecular weight of 15 000 g/mol to 150 000 g/mol and random branches of PDA with a mass content of about 3-, or 5 wt. %.

In yet another embodiment, the present invention provides a polymer of the formula (I)

$$HO-[(CH_2)_4-CH(PDA)-C(O)-O]_r-(CH_2)_5-[C(O)-O]_p-H \qquad (I)$$

wherein p=23-1580 and r=1-395; and wherein the PDA is present in up to 5 wt. %; or in about 3 to 5 wt. %, or in about 3 or 5 wt. %.

In another embodiment, the present invention provides methods for making the present graft copolymers. In one embodiment, the PCL backbone is first chemically modified, for example iodized, and is subsequently reacted with a suitable PDA precursor to give the copolymers in accordance with the present invention. Any suitable PDA precursor know to the person of skill in polymer chemistry can be used. In one embodiment the PDA precursor is dopamine hydrochloride. The polymerization takes place according to conditions known to the skilled person and as further disclosed in the accompanying working examples. In one embodiment, the polymerization is carried out under oxidative and basic conditions to yield PDA-grafted PCL (PCL-g-PDA) [7], which are subsequently further purified.

Therefore, the present invention provides a method for making the present PCL-g-PDA copolymers, characterized in that PCL with molar percentage of iodized PCL units in the range 0.1 to 50 mol. %; or 1 to 20 mol. %, is reacted with a PDA precursor, for example dopamine hydrochloride. In one aspect this method is carried out under oxidative and basic conditions and in the presence of copper(I) bromide at about 70° C. under inert atmosphere. The so obtained graft copolymers are purified. Purification can be carried out according to methods known to the skilled person and/or as described in the accompanying working examples. In one embodiment purification is carried out by precipitation, preferably by precipitation from methanol. The precipitation steps can be repeated several times, preferably up to three times. In yet another embodiment purification is carried out by precipitation from methanol, followed by 2 times trituration of the PCL-g-PDA from cold methanol.

In one embodiment, the method for making the present PCL-g-PDA copolymers is as disclosed in the accompanying working examples or as disclosed in schemes 1 and 2, using specific starting materials, intermediates and reaction conditions disclosed therein.

In another embodiment the present invention discloses a PCL-g-PDA co-polymer obtained by using the methods disclosed herein, especially the methods disclosed in schemes 1 and 2.

Iodized PCL can be obtained using methods know to the skilled artisan, and as for example described in [6]. In one embodiment, iodized PCL is obtained according to the method disclosed in scheme 1 and in the accompanying working examples. In yet another embodiment, the present invention provides functionalization of said PCL by post modification. In a preferred embodiment in accordance with the present invention PCL with a high molecular weight, i.e. above 45 000 g/mol, is iodized. The use of such high molecular weight PCL is advantageous to develop degradable solid preparations, combining synthesis feasibility and good mechanical properties of the resulting implants in the sense that the implants are more flexible and less brittle.

The PCL-g-PDA copolymers according to the present invention have valuable pharmaceutical properties. In particular, they have been found to be stable, well tolerated and suitable for sustained release of pharmaceutically active ingredients.

Therefore, in another embodiment, the present invention provides the present copolymers for use in pharmaceutical preparations, for example as a carrier for active pharmaceutical ingredients. In one aspect, in accordance with the present invention, said pharmaceutical preparations are implants. In another aspect said implants are suitable for use in the eye, for example, as intravitreal implants. In another aspect said implants can further contain another polymer such as, for example, PCL or PLA or PLGA together with the active ingredient. In yet another aspect, the intravitreal implants only consist of the present copolymer together with a suitable active ingredient.

The term active pharmaceutical ingredient as used herein means any molecule with a clinically meaningful pharmacological activity. In one embodiment, an active pharmaceutical ingredient is a small molecule, as defined by Lipinski's rule of five. In another embodiment, an active pharmaceutical ingredient is a drug which is approved for the treatment of ocular diseases such as, for example, glaucoma, cataract, age-related macular degeneration, diabetic retinopathy and uveitis. In another embodiment, the active pharmaceutical ingredient is selected from the group consisting of ganciclovir, dexamethasone, fluocinolone acetonide, and cyclosporine A.

In accordance with the present invention, the active pharmaceutical ingredient is present in the implant in an amount not less than 10 weight %, or from 10 to 60 weight %, or from 10 to 30 weight %.

In another embodiment, the present invention provides the use of the present copolymer for the preparation of medicaments such as, for example, implants for the treatment of ocular diseases; or for intravitreal administration of drugs. In one aspect such administration is a sustained release over time periods as defined herein.

In another embodiment, the present invention provides a method for treating ocular diseases by placing an implant comprising a copolymer of the present invention loaded with a suitable active pharmaceutical ingredient, or approved drug, into the eye of a patient in need of such treatment.

described in Scheme 1. The first step is the anionic activation of PCL in presence of LDA, the second step is the electrophilic substitution of iodine.

Scheme 1: Synthesis scheme of iodized PCL (PCL-I), with n = 43-1755; p = 23-1580 and q = 2-395.

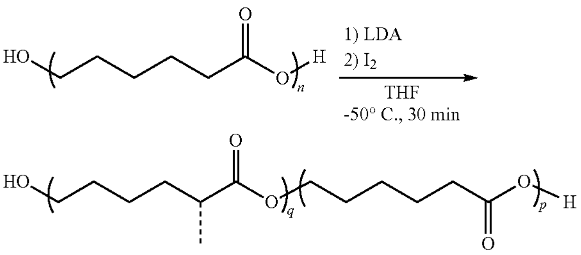

Starting from commercial PCL, a series of iodinated PCL were prepared by targeting different molecular weights and copolymer masses, and were characterized by SEC and $^1H$ NMR. The results are summarized in Table 1.

TABLE 1

Characterizations of iodinated PCL (PCL-I) prepared in THF by anionic activation using LDA and electrophilic substitution using iodine.

| | PCL | | | PCL-I obtained after reaction | | | | |
|---|---|---|---|---|---|---|---|---|
| Assay | $M_n$ [a] (g/mol) | Đ [a] | Mass of PCL (g) | $M_n$ [a] (g/mol) | Đ [a] | Mass of PCL-I (g) | Iodation ratio ($T_I$) [b] (mol %) | Molar yield ($\eta_x$) (g) |
| I1 | 43 100 | 1.62 | 5 | 17 100 | 2.56 | 3.9 | 11 | 70 |
| I2 | 127 000 | 1.61 | 5 | 27 000 | 3.60 | 4.2 | 11 | 75 |

[a] determined by SEC in THF using PS standards for calibration;
[b] determined by $^1H$ NMR in $CDCl_3$ In a second step, PCL-g-PDA is obtained according to the following reaction scheme 2, based according to the conditions adapted from Cho et al.[7]:

Scheme 2: Synthesis of PCL-g-PDA, with p = 23-1580; q = 2-395 and r = 1-395

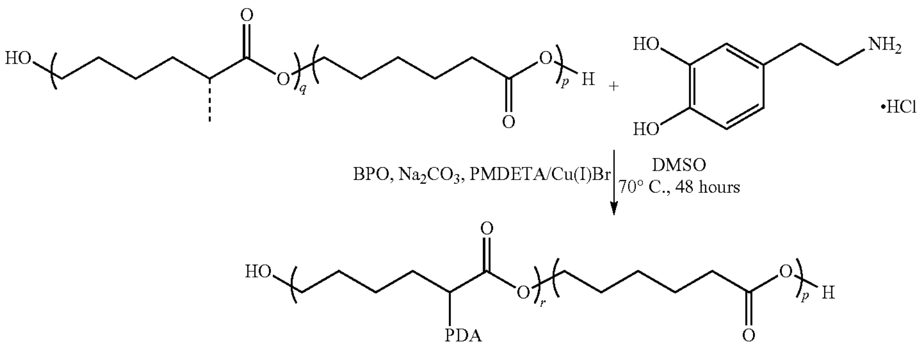

General Synthesis of PCL-g-PDA

The PCL-g-PDA copolymers of the present invention can be obtained using the following general reaction schemes. In a first step, iodinated PCL is obtained by post modification of PCL by iodine. The post modification method of functionalisation of PCL is based on the work of Nottelet et al.[6] The method consists in a two-step one-pot reaction In brief, Dopamine was introduced in a Schlenk flask containing DMSO, sodium carbonate, BPO and PMDETA at room temperature. Sodium carbonate is used to obtain basic conditions. BPO is an organic peroxide frequently used as radical initiator to induce chain-growth polymerization, PDMETA (also written PMDTA) is a tridentate ligand which can bind to metallic cation to form a complex. Rapidly after introduction of all those components (in less than one minute), the solution turned from white to black, suggesting the oxidative polymerization of dopamine. Meanwhile, PCL-I was solubilized in DMSO at room temperature. The solutions were stirred during 4 hours. The PCL-I macroinitiator solution was transferred to the first solution, and copper(I) bromide was added. Copper (I) bromide is a metallic agent that binds to the ligand and allows, like in ATRP, to activate the PCL-I dormant macroinitiator to generate a free radical PCL which was coupled with dopamine monomer or already grown PDA. The solution was heated at 70° C. during 48 hours, then cooled by diving into liquid nitrogen. The majority of the solvent was removed by evaporation, then the solution was precipitated in methanol to collect the final copolymer. During precipitation, methanol turned black suggesting the presence of non-grafted PDA in the solution of DMSO, and that non-grafted PDA compounds were further solubilized in methanol.

Therefore, in another embodiment the present invention provides a method for making PCL-g-PDA, wherein said method comprises the reaction sequence, including starting materials, intermediates, reaction partners and—conditions as described in schemes 1 and 2 herein.

Materials and Methods

Chemicals and Materials

Poly(ethylene glycol) (PEG), toluene, diethyl ether, methanol, dichloromethane (DCM), tetrahydrofurane (THF), poly(ε-caprolactone) (PCL), iodine, hydrochloric acid (HCl, 37%), lithium diisopropylamide (LDA), sodium thiosulfate, benzene dimethanol, ε-caprolactone (εCL), stannous octanoate ($Sn(Oct)_2$), dimethyl sulfoxide (DMSO), dopamine hydrochloride, benzoyl peroxide (BPO), copper (I) bromide, N,N,N',N',N"-pentamethyldiethylenetriamine (PMDETA) and ciprofloxacin hydrochloride (CIP.HCl) were purchased from Sigma-Aldrich. Ammonium chloride, polysorbate 20 (Tween 20), were purchased from Acros Organics. Carbonate sodium was purchased from Fisher Scientific. Dexamethasone (DEX) was purchased either from Sigma Aldrich or TCI.

Characterizations

Nuclear Magnetic Resonance (NMR)

Proton nuclear magnetic resonance spectroscopy ($^1H$-NMR) was carried out to determine functionalization ratio of the polymer using a Bruker AMX-400 MHz spectrometer in either $CDCl_3$ or DMSO-$d_6$ for iodized PCL. Diffusion ordered spectroscopy NMR (DOSY NMR) was carried out to highlight separate coefficients of diffusion of the species contained in the sample and determine the presence of residual free-species. Sample concentration was from 5 to 15 mg/mL.

Size Exclusion Chromatography (SEC)

SEC THF: Samples (5 mg/ml) were filtrated through a 0.45 μm PTFE Millipore filter and analysed using a Shimadzu (Japan) apparatus equipped with a RID-20A refractive index signal detector, a SPD-20A UV/VIS detector, a PLgel MIXED-C guard column (Agilent, 5 μm, 50×7.5 mm), and two PLgel MIXED-C columns (Agilent, 5 μm, 300×7.5 mm). The mobile phase was THF with a flow rate of 1.0 mL·min$^{-1}$. The injection volume was 100 μL. The average molecular weights and dispersities (Đ) were calculated using polystyrene (PS) as standard.

SEC DMSO: PCL-g-PDA copolymers (1 mg/mL) were filtrated through a 0.45 μm PTFE Millipore filter and analysed using a Waters 515 HPLC apparatus equipped with a Waters 410 differential refractometer, a Waters 2996 photodiode array detector, a Polargel-M guard column (Agilent, 50×7.5 mm), and two Polargel-M columns (Agilent, 300×7.5 mm). The mobile phase was DMSO with a flow rate of 1.0 mL/min. The injection volume was 50 μL. The quantification of PDA content was determined by the area ratios between the copolymer containing PDA and the oligo PDA itself at a specific wavelengths chosen in the range from 254 to 400 nm.

In both of the above described SEC methods, when analysing the PCL-g-PDA copolymers, DMF can also be used as mobile phase under the conditions described.

Thermogravimetric Analysis (TGA)

Thermal decomposition of the copolymers (from 0.1 to 10 mg) was studied using a thermogravimetric analyser (TGA Q500 v20.13 build 39). Samples were heated from 30° C. to 700° C. at 20° C./min under nitrogen atmosphere.

Differential Scanning Calorimetry (DSC)

Samples (from 1 to 10 mg) of each copolymer were placed in an aluminum pan. Samples were heated from −80° C. to 300° C. at 10° C./min using a Mettler Toledo DSC 3. The glass transition temperature and melting temperature of each sample were determined during the first heating cycle. The melting enthalpies were used to calculate crystallinities (X) using the reference value of ΔH=139,5 J/g for crystalline PCL [8].

High Performance Liquid Chromatography (HPLC)

Samples were filtrated through a 0.45 μm PTFE Millipore filter and analysed using a Shimadzu (Japan) apparatus equipped with a SPD-M20A diode array detector, and a HPLC C18 column (Kinetex, 2.6 μm, 100A, 100×4.6 mm). An isocratic mode was applied to detect drugs, 40% ACN (0.1% TFA)+60% $H_2O$ (0.1% TFA) for the detection of DEX and 13% ACN (0.1% TFA)+87% $H_2O$ (0.1% TFA) for the detection of CIP. After detection, column was washed using a linear gradient until 100% ACN. The flow rate was 1.0 mL/min.

Chapter II: (PCL-g-PDA)-b-PEG-b-(PCL-g-PDA)

The in-situ gelling system approach in accordance with the present invention provides amphiphilic grafted copolymers of the type (PCL-g-PDA)-b-PEG-b-(PCL-g-PDA), based on the knowledge gained in Chapter I. Firstly, amphiphilic triblock PCL-b-PEG-b-PCL were synthesized at various PEG and PCL chain lengths to generate an in-situ forming gel at physiological temperature in water. In one embodiment PEG has a molecular weight up to 20000 g/mol. In another embodiment, PEG has a molecular weight from 1000 to 4600 g/mol. In yet another embodiment, triblock copolymer with different chain lengths of PEG and PCL, but same chain lengths for each PCL, are provided in order to obtain EG/CL ratios ranging from 0.30 to 2.13 and molecular weights from 4 300 to 9 400 g/mol. In yet another embodiment, the two PCL chains have a molecular weight between 846 and 2100 g/mol and the PEG chain has a molecular weight between 1000 and 4600 g/mol. In yet another embodiment, the two PCL chains have a molecular weight of 855 or 890 g/mol and the PEG chain has a molecular weight of 2000 g/mol. These two specific PCL-b-PEG-b-PCL showed good gelling capacity at room temperature.

The PCL-b-PEG-b-PCL with 855-2000-855 (g/mol) distribution was functionalized via iodine by an electrophilic substitution to give (PCL-I)-b-PEG-b-(PCL-I), which was further functionalized by PDA under ATRP-like, oxidative and basic conditions. The raw (PCL-g-PDA)-b-PEG-b-(PCL-g-PDA) contained about 40 wt. % of PDA including some free (not grafted) PDA.

General Synthesis of (PCL-g-PDA)-b-PEG-b-(PCL-g-PDA)

The copolymers of the type (PCL-g-PDA)-b-PEG-b-(PCL-g-PDA) (also designated "T-PDA" herein) in accordance with the present invention (Chapter II) can be synthesized based on the following general reaction schemes 3 to 5.

Scheme 3: Synthesis of PCL-b-PEG-b-PCL (m = 22-455, n = 3-568)

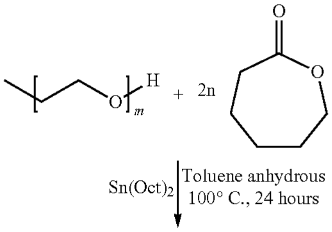

-continued

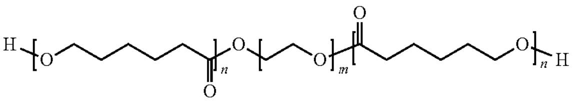

The triblock copolymers PCL-b-PEG-b-PCL (also designated "T" herein) are synthesized by ring opening polymerization (ROP) in anhydrous toluene of ε-CL using commercial PEG-diols as initiator (Scheme 3) and $Sn(Oct)_2$ as catalyst. The solution is stirred during 24 hours at 100° C. and precipitated in cold diethyl ether, filtrated and dried under vacuum.

The post-polymerization modification leading to the functionalisation of PCL with Iodine is based on the work described by Nottelet et al. [6] and is similar to the method presented in Chapter I. The method consists of a two-step one-pot reaction described in Scheme 4.

Scheme 4: Synthesis of (PCL-I)-b-PEG-b-(PCL-I) (m = 22-455; n = 3-568; p = 3-397 and q = 1-170)

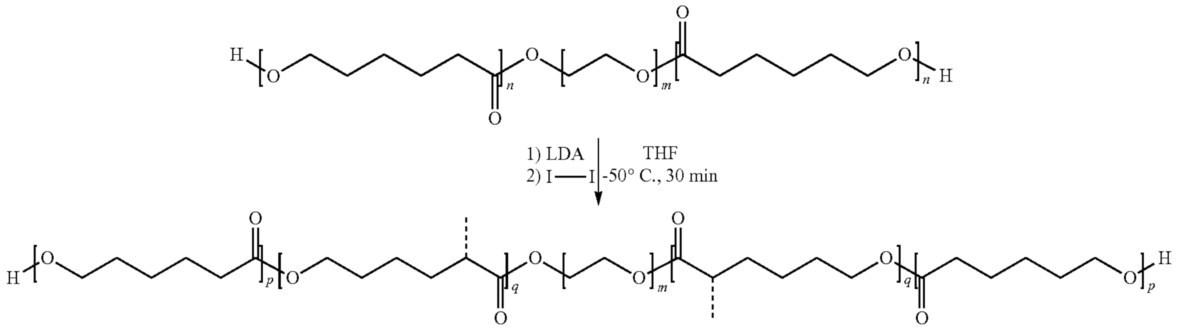

The first step is the anionic activation in presence of LDA of the most electrophilic proton of the PCL backbone, the second one is the electrophilic substitution with iodine. The resulting polymer of the type (PCL-I)-b-PEG-b-(PCL-I) is also designated "T-I" herein.

Finally, the functionalization of T-I with PDA was carried out in conditions similar to those described in Chapter I. The reaction scheme is shown in Scheme 5 and detailed conditions have also been described in Example 9.

Scheme 5: Synthesis of (PCL-g-PDA)-b-PEG-b-(PCL-g-PDA) ("T-PDA"; p = 3-397; m = 1-170 and r = 1-170)

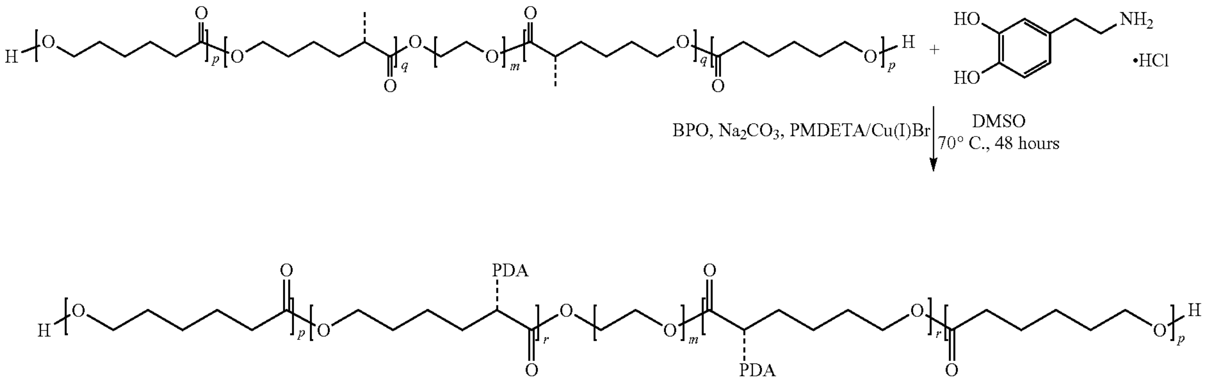

For purification, the solution of DMSO containing T-PDA was precipitated in cold diethyl ether but T-PDA was stuck to the bottom complicating the collection of the product. In a second step, the solution of DMSO containing T-PDA was introduced into a dialysis bag and DMSO was exchanged with water to collect T-PDA. Dialysis was kept as preferential purification method at this stage to collect T-PDA for further analysis. T polymers containing PDA (T-PDA) are new type of copolymers and are one embodiment of the present invention.

Therefore, in one embodiment, the present invention provides a PCL-g-PDA copolymer as defined herein (Chapter I) wherein two PCL-g-PDA chains are attached to a PEG chain in order to give grafted copolymers of the type (PCL-g-PDA)-b-PEG-b-(PCL-g-PDA). In one aspect, the PEG chain has a molecular weight as defined herein, and the two PCL-g-PDA chains both have the same molecular weight.

In another embodiment, the present invention provides a polymer of the T-PDA type as defined herein, of formula (II)

The term active pharmaceutical ingredient used in connection with the T-PDA copolymers means any molecule with a clinically meaningful pharmacological activity, preferably an antibody. The term "antibody" herein is used in the broadest sense and encompasses various antibody classes or structures, including but not limited to monoclonal antibodies (mAb), polyclonal antibodies, multispecific antibodies (e.g., bispecific antibodies), and antibody fragments so long as they exhibit the desired antigen-binding activity. In one embodiment, the antibody is a monoclonal, mono- or bispecific antibody or an antigen-binding fragment thereof. In one embodiment, the antibody is human or humanized. In another embodiment, the antibody is any of the aforementioned antibodies which can be used to treat ocular diseases. In yet another embodiment, the antibody is the molecule with the INN faricimab.

In accordance with the present invention, the active pharmaceutical ingredient is present in the depot in an amount up to 45 wt. %; or from 5 to 45 wt. %; or from 15 to 45 wt. % or form 20 to 45 wt. %, wherein the wt. % is with respect to T-PDA;

(II)

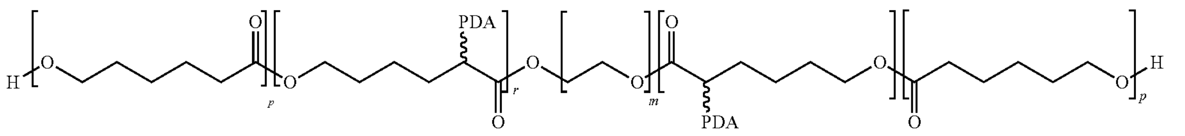

wherein
p is 3 to 397
r is 1 to 170
m is 1 to 170.

The present invention also provides methods for making the new T-PDA polymers. In one embodiment the present invention provides a method for making polymers of the T-PDA type, wherein said method comprises the reaction sequence, including starting materials, intermediates, reaction partners and—conditions as described in schemes 3 to 5 herein.

In another embodiment, the present invention also provides the T-PDA polymers obtained when using the reaction sequence (starting materials, intermediates and conditions) in accordance with schemes 3 to 5 herein.

The T-PDA copolymers according to the present invention, for example of formula (II), have valuable pharmaceutical properties. In particular, they have been found to be stable, well tolerated and suitable for sustained release of pharmaceutically active ingredients.

Therefore, in one embodiment, the present invention provides the T-PDA copolymers as defined herein, for example of formula (II), for use in pharmaceutical preparations, for example as a carrier for active pharmaceutical ingredients. In one aspect, in accordance with the present invention, said pharmaceutical preparations are depots formed by in situ gelation. In another aspect said in situ formed depots are suitable for use in the eye, for example, for intravitreal injection. In yet another aspect this pharmaceutical preparation forms an in situ gelling depot for sustained release of said active pharmaceutical ingredient upon injection in the eye. In still another aspect in accordance with the present invention said pharmaceutical preparation is an aqueous solution, or a suitable buffer such as, for example, Histidine buffer solution, comprising the T-PDA copolymer together with the active pharmaceutical ingredient and further comprising PEG as co-solvent, preferably PEG400 as defined herein.

In another embodiment, the present invention provides the use of the present T-PDA copolymers, for example of formula (II), for the preparation of medicaments. In one aspect such medicaments are for the treatment of ocular diseases; or for intravitreal administration of drugs.

In another embodiment, the present invention provides a method for treating ocular diseases by injecting a pharmaceutical preparation comprising a T-PDA copolymer of the present invention loaded with a suitable active pharmaceutical ingredient, or approved drug, into the eye of a patient in need of such treatment. In one aspect the injection is an intravitreal injection.

In another embodiment, an aqueous formulation containing PCL-b-PEG-b-PCL and/or (PCL-g-PDA)-b-PEG-b-(PCL-g-PDA) and a monoclonal antibody (mAb) is provided. In one aspect this formulation further comprises a soluble co-solvent, preferably PEG400. In yet another aspect the present invention provides a formulation composed of histidine buffer (HBS) and PEG400 (ratio HBS:PEG400=1:1 or 1:2) as solvent, containing 5 to 15, preferably 5 or 10 wt. % of PCL-b-PEG-b-PCL or (PCL-g-PDA)-b-PEG-b-(PCL-g-PDA) and loaded with 40 mg/mL of mAb. In one aspect, these formulations are injectable through a 30G needle. The stability study of mAb showed the ability of (PCL-g-PDA)-b-PEG-b-(PCL-g-PDA) to interact with mAb without causing its denaturation during 30 days. In vitro, these formulations formed an in-situ gelling depot by solvent-exchange process.

The term "PEG" as used herein, especially for embodiments in Chapter II, means poly(ethylene glycol). In accordance with the present invention PEG of different molecular weights can be used. In one embodiment PEG has a molecular weight of up to 20 000 g/mol. In another embodiment PEG has a molecular weight of 400; or 1000; or 1450; or 2000; or 4600; or 10000; or 20000 g/mol.

Specifically for Chapter II, the molecular weight of each polymer will be written in index number. For example, PEG of 1000 g/mol will be defined as PEG1000 and PCL of 2000 g/mol will be defined as PCL2000. Across the specification, copolymers of the type PCL-b-PEG-b-PCL, for example with PEG of 1000 g/mol and each PCL of 2000 g/mol can also be designated as 1000-2000-1000.

Unless explicitly mentioned, terms defined in Chapter I have the same meaning when used in connection with the embodiments as defined in Chapter II.

Materials and Methods

Many of the materials mentioned herein for the preparation of the PCL-g-PDA copolymers and implant based thereon (Chapter I) can also be used for the preparation of the tri-block-copolymers in this Chapter II, with addition of poly(ethylene glycol) (PEG, Mn 400 or 1 000 or 1 450 or 2 000 or 4 600 or 10 000 or 20 000 g/mol), toluene, stannous octanoate ($Sn(Oct)_2$), ε-caprolactone (ε-CL), and diethyl ether that were purchased from Sigma-Aldrich. PEG was dried by azeotropic distillation of toluene solutions of PEG, and ε-CL was dried over calcium hydride (CaH2) for 48 h at room temperature and distilled under reduced pressure-.before use. PEG, ε-CL and $Sn(Oct)_2$ were kept under argon atmosphere.

Characterization

Nuclear magnetic resonance spectroscopy (NMR spectroscopy), Size Exclusion Chromatography (SEC) using THF as mobile phase, Differential Scanning calorimetry (DSC), Thermogravimetric analysis (TGA) methods and instruments are similar to the ones described in Chapter I.

Size Exclusion Chromatography (SEC) using DMF as Mobile Phase

The number-average and weight-average molar masses (Mn and Mw, respectively) and dispersity (Đ, Mw/Mn) of the polymers were determined by SEC. The samples (5 mg/ml) were filtrated through a 0.45 μm PTFE Millipore filter and analyzed using a Shimadzu (Japan) apparatus equipped with a RID-20A refractive index signal detector coupled to a SPD-20A UV/VIS detector and to a PLgel MIXED-C guard column (Agilent, 5 μm, 50×7.5 mm) and two PLgel MIXED-C columns (Agilent, 5 μm, 300×7.5 mm). The mobile phase was DMF+0.1% LiBr. The flow rate was 1.0 mL·min-1 and the injection volume was 100 μL. The average molecular weight and dispersity (Đ) were express according to calibration using poly(ethylene glycol) (PEG) standards.

Aqueous Size Exclusion Chromatography (Aqueous SEC)

The samples (1 mg/ml) were filtrated through a 0.20 μm RC Millipore filter and analyzed using a Shimadzu (Japan) apparatus equipped with a RID-20A refractive index signal detector coupled to a SPD-40 UV/VIS detector and to a Biobasic SEC 300 guard column (Thermo Scientific, 5 μm, 20×8 mm) and one Biobasic SEC 300 column (Thermo Scientific, 5 μm, 150×7.8 mm). The mobile phase was an aqueous buffer solution composed of HK2PO4/KH2PO4 (0.1 M, pH=7). The flow rate was 0.80 mL·min-1 and the injection volume was 100 μL.

Injectability Testing by Compression Measurements

Injectability tests were carried out using a Instron 3344 with a 500N captor in compression mode. In the study, hypodermic needles (Sterican® for special indications, B. Braun, Germany) in sizes 27G-30G and 1 mL disposable syringes (Omnifix®-F Luer, B.Braun, Gremany) were used. The syringes were filled with 1 mL of solution then the hypodermic needles were attached. The speed of injection was set at 0.5 or 1 mm/s and the volume of injection was 100 μL corresponding to a displacement of the plunger of 6 mm. The surrounding media was air.

References (1) Pascolini, D.; Mariotti, S. P. Global Estimates of Visual Impairment: 2010. *Br J Ophthalmol* 2012, 96 (5), 614-618. https://doi.org/10.1136/bjophthalmol-2011-300539.

(2) Yasin, M. N.; Svirskis, D.; Seyfoddin, A.; Rupenthal, I. D. Implants for Drug Delivery to the Posterior Segment of the Eye: A Focus on Stimuli-Responsive and Tunable Release Systems. *Journal of controlled release: official journal of the Controlled Release Society* 2014, 196, 208-221. https://doi.org/10.1016/j.jconrel.2014.09.030.

(3) Liebscher, J.; Mrówczyński, R.; Scheidt, H. A.; Filip, C.; Hădade, N. D.; Turcu, R.; Bende, A.; Beck, S. Structure of Polydopamine A Never-Ending Story? *Langmuir: the ACS journal of surfaces and colloids* 2013, 29 (33), 10539-10548. https://doi.org/10.1021/la4020288.

(4) Rimpelä, A.-K.; Reinisalo, M.; Hellinen, L.; Grazhdankin, E.; Kidron, H.; Urtti, A.; Del Amo, E. M. Implications of Melanin Binding in Ocular Drug Delivery. *Advanced drug delivery reviews* 2018, 126, 23-43. https://doi.org/10.1016/j.addr.2017.12.008.

(5) Liu, X.; Cao, J.; Li, H.; Li, J.; Jin, Q.; Ren, K.; Ji, J. Mussel-Inspired Polydopamine: A Biocompatible and Ultrastable Coating for Nanoparticles in Vivo. *ACS nano* 2013, 7 (10), 9384-9395. https://doi.org/10.1021/nn404117j.

(6) Nottelet, B.; Coudane, J.; Vert, M. Synthesis of an X-Ray Opaque Biodegradable Copolyester by Chemical Modification of Poly (ε-Caprolactone). *Biomaterials* 2006, 27 (28), 4948-4954. https://doi.org/10.1016/j.biomaterials.2006.05.032.

(7) Cho, J. H.; Shanmuganathan, K.; Ellison, C. J. Bioinspired Catecholic Copolymers for Antifouling Surface Coatings. *ACS applied materials & interfaces* 2013, 5 (9), 3794-3802. https://doi.org/10.1021/am400455p.

(8) Pitt, C. G.; Chasalow, F. I.; Hibionada, Y. M.; Klimas, D. M.; Schindler, A. Aliphatic Polyesters. I. The Degradation of Poly(ϵ-Caprolactone) in Vivo. *J. Appl. Polym. Sci.* 1981, 26 (11), 3779-3787. https://doi.org/10.1002/app.1981.070261124.

Overall, the present invention provides new PDA-based biomaterials to respond to the challenges of minimally invasive long-acting ocular delivery using biocompatible degradable synthetic copolymers. It provides PDA-based implants suitable for the long-term delivery of small molecules and PDA-based injectable in situ gelling system promising for the formulation of biologics. The invention will now be further illustrated by the following working examples, which are in no way meant to limit the scope of the present invention.

EXAMPLES

Example 1. Synthesis of Initiators and Precursors

Synthesis of the diethylene glycol bis(2-bromoisobutyrate)

In a typical experiment, diethylene glycol (1 g, 9.42 mmol), triethyl amine (3.94 mL, 28.3 mmol) and dry THF (40 mL) were added in a dry three-neck round-bottom flask and placed in an ice bath. Then, isobutyryl bromide (3.49 mL, 28.3 mmol) was slowly added into the flask through a dropping funnel. A guard tube filled with calcium chloride was placed to keep anhydrous conditions. Solution was left under stirring overnight. Solution was filtrated over diatomaceous earth and concentrated by evaporating THF. The crude product was dissolved in a mix of water and dichloromethane. The product was extracted from the solution by washing three times with dichloromethane using a separative funnel. The organic phase was dried using MgSO4 powder, filtrated and dried under reduced pressure. The product was purified by filtration over silica using a mix of ethyl acetate:heptane (30:70) as solvent. Fractions were collected and evaporated under reduced pressure. Pure fractions were gathered and stocked at 4° C. for further use.

Yield: 100 mol. %

1H NMR (300 MHz, CDCl3): δ=4.28 (t, R—CH2-O—CO), 3.73 (t, O—CH2-R), 1.89 (s, R—CH3)

Synthesis of PDA Oligomers

In a typical experiment, dopamine hydrochloride (1.5 g, 7.91 mmol), PMDETA (130 μL, 0.63 mmol), Na2CO3 (402.0 mg), BPO (1.92 g, 7.91 mmol), and DMSO (76 mL) were added. Solution was left under stirring and argon flux for 4 hours. Then, oxygen was removed by three freeze-pump thaw cycles. Diethylene glycol bis(2-bromoisobutyrate) (0.13 g, 0.32 mmol) and copper(I) bromide (0.09 mg, 0.63 mmol) were added. The flask was then dived in an oil bath at 70° C. and the reaction was carried out under vigorous stirring for 48 hours. Reaction was stopped by cooling in a liquid nitrogen bath. Solution was then concentrated by evaporating DMSO at 70° C. under vacuum. Finally, the polymer was precipitated, filtrated and dried under vacuum.

Yield: 17 wt. %

1H NMR (600 MHz, DMSOd6): δ=6.30-7.00 ppm (m, PDA)

Synthesis of Iodized Poly(ε-caprolactone)

PCL backbone was anionically activated using LDA then modified by iodine after electrophilic substitution. For this synthesis, PCL (3 g, $M_{n,SEC,THF}$=65 000 g/mol, 26.3 mmol of CL units) and anhydrous THF (300 mL) were introduced into a dry conic reactor, and put under argon atmosphere until complete PCL dissolution. The solution was then cooled down at −50° C. by diving it into a liquid nitrogen/ethanol mixture before addition of LDA (13.16 mL, 1 eq. with respect to εCL unit, 26.3 mmol) under argon. After 30 minutes of reaction, a solution of iodine (6.68 g, 1 eq. with respect to εCL unit, 26.3 mmol) in a minimum amount of anhydrous THF was injected with a syringe through a septum and the mixture was kept at −50° C. under stirring and argon atmosphere. After 30 minutes the reaction was stopped by addition of an aqueous solution of $NH_4Cl_{(aq)}$ (2 M, 200 mL) and the temperature was increased to 0° C. prior to addition of HCl (aq) (37%) to reach a neutral pH. The polymer was extracted from the solution by washing three times with dichloromethane (3×200 mL) in a separating funnel. Organic phases were collected, washed three times with a solution of $Na_2S_2O_3$ (3×100 mL, in excess), dried using $MgSO_4$ powder, filtrated and concentrated under reduced pressure using a rotatory evaporator. The polymer was precipitated in cold methanol, filtrated and dried under vacuum.

Characterisations:

$^1$H NMR in $CDCL_3$: determination of the functionalization ratio (FIG. 1): $^1$H NMR ($CDCl_3$, 300 MHz, ppm): 4.30 (m, R—CHI—CO), 4.05 (t, R—$CH_2$—O—CO), 2.30 (t, R—$CH_2$—CO—O), 2.00 (t, R—$CH_2$—CHI), 1.64 (m, R—$CH_2$—C—CO), 1.38 (m, R—$CH_2$—R)

SEC in THF: determination of the number average molecular weight (FIG. 2).

Results:

The substitution degree was calculated by comparison between the integrals of the resonance peaks at 4.30 ppm, corresponding to the vicinal proton of the iodine, and at 4.05 corresponding to the non-substituted methylene group (FIG. 1, Table 2).

TABLE 2

Results of the modification of commercial PCL by iodine after precipitation in methanol. [εCL]/[LDA]/[$I_2$] =1/1/1. $m_{PCL}$ = 5 g.

| $M_{n, PCL, SEC}$ [b] (g/mol) | $Đ_{PCL}$ [b] | PCL-I Sample | $M_{n, PCL-I, SEC}$ [b] (g/mol) | $Đ_{PCL-I}$ [b] | $T_I$ [a] (mol %) |
|---|---|---|---|---|---|
| 43 100 | 1.62 | FB54 | 17 100 | 2.56 | 11 |
| 64 700 | 1.67 | FB86 | 29 200 | 3.69 | 10 |

[a] determined by $^1$H NMR in $CDCl_3$, using the integration of the peak at 4.30 ppm and the peak at 4.05 ppm as reference

[b] determined by SEC in THF using PS standards for calibration (FIG. 2).

Example 2: Synthesis of PCL-graft-PDA

Typically, in a Schlenk flask A, iodized PCL (1.5 g, 1.18 mmol of iodized CL units) and DMSO (20 mL) were added. In a Schlenk flask B, Dopamine-HCl (5.62 g, 25 eq. with respect to iodized CL unit, 29.6 mmol), PMDETA (370 μL, 1.5 eq. with respect to iodized CL unit, 1.78 mmol), $Na_2CO_3$ (300.0 mg), BPO (7.18 g, 25 eq. with respect to iodized CL unit, 29.6 mmol), and DMSO (37 mL) were added. Solutions were left under stirring and argon flux for 4 hours. Then, oxygen was removed by three freeze-pump thaw cycles. Iodized PCL solution was transferred to the flask B and copper(I) bromide (255 mg, 1.5 eq. with respect to iodized CL, 1.78 mmol) was added. The flask was then dived in an oil bath at 70° C. under inert atmosphere and vigorous stirring during 48 hours. Reaction was stopped by cooling in a liquid nitrogen bath. Solution was concentrated by evaporating DMSO at 110° C. under vacuum. The copolymer was precipitated in methanol, filtrated and dried under vacuum.

Characterisations:

$^1$H NMR in DMSO-$d_6$: highlight of the chemical modification and the purity of the graft copolymer (FIG. 3).

DOSY NMR in DMSO-$d_6$: confirmation of grafting with peak at 4.58 ppm (FIG. 4).

SEC in DMSO (UV at λ=350 nm): confirmation of the presence of PDA in the copolymer (FIG. 5).

TGA: quantification of PDA content (FIG. 6).

DSC: determination of the melting temperature of the copolymer (FIG. 7).

Results:

In the $^1$H NMR the peaks at 4.58, 1.90 and 1.80 ppm is characteristic from iodized PCL modification in basic conditions (FIG. 3) resulting from the grafting onto PCL (FIG. 4). In UV-SEC analysis, PCL-g-PDA copolymer and PDA absorb from 254 to 450 nm (FIG. 5). We selected 350 nm as wavelength to avoid residual noise. The peak intensity is proportional to the PDA content. The PDA content was also measured by TGA analysis (FIG. 6). The melting temperature of PCL-g-PDA is 49° C. as determined on the first heating ramp by DSC analysis (FIG. 7). A summary of the results can also be found in Table 3, below.

TABLE 3

Characteristics of PCL-g-PDA copolymers after purification in methanol as a function of the initial molecular weight and the substitution degree of iodized PCL.

| PCL-I used for reaction | | | | PCL-g-PDA copolymer obtained after reaction | | | |
|---|---|---|---|---|---|---|---|
| PCL-I Sample | $M_{n,PCL-I,SEC}$ [b] (g/mol) | $Đ_{PCL-I}$ [b] | $T_I$ [a] (%) | PCL-g-PDA Sample | PDA content [c] (wt %) | $M_{n,PCL-g-PDA,SEC}$ [d] (g/mol) | $Đ_{PCL-g-PDA}$ [d] |
| FB162 | 21 400 | 3.15 | 10 | FB163 | 3 | 46 000 | 2.73 |
| FB164 | 20 500 | 3.05 | 12 | FB165 | 5 | — | — |

[a]determined by $^1H$ NMR in DMSO-d6;
[b] determined by SEC in THF using PS standards for calibration;
[c] determined by TGA after 3 purification steps;
[d] determined by SEC in DMF using PS standards for calibration The quantification of PDA content by TGA is based on the remaining masses at 600° C. of PCL, PCL-g-PDA and oligo-PDA, using the apparatus as described herein. The PDA content is then calculated using the following equation:

$$W\ \%_{PDA\ in\ copolymer} = \frac{\%_{remaining\ mass\ in\ PCL-g-PDA\ at\ 600^\circ C.} - \%_{remaining\ mass\ in\ PCL\ at\ 600^\circ C.}}{\%_{remaining\ mass\ in\ oligo-PDA\ at\ 600^\circ C.}} * 100$$

The proportion of PDA in the PCL-g-PDA copolymer purified three times was about 3 wt. %.

An alternative way of purification involves trituration from cold methanol: After a first purification step by precipitation from methanol, the copolymer can be further purified by trituration from cold methanol. More specifically, 300 mg of copolymer are placed in a falcon tube. 45 mL of cold methanol are added and the polymer powder is triturated for few minutes before recovering it by centrifugation (0° C., 5000 rpm, 15 min). This step is repeated once more before drying. (Trituration step yield=50%.)

The data disclosed herein, especially in Table 3, did not involve trituration but only precipitation from methanol.

Example 3: Preparation of Drug-Loaded Implants

PCL (Mn about 60 000 g/mol) or PCL-g-PDA (from 100 to 500 mg), obtained in Example 2, and appropriate amounts of DEX or CIP.HCl (corresponding to 10 and 30% of final weight) were dispersed in DMSO (from 5 to 30 mL) to allow intimate mixing. DMSO was removed at 110° C. under vacuum to yield a copolymer/drug thin film. The film is ground and the resulting powder was deposed on a Teflon sheet. The powder was pressed during 15 min under 4 tons at 130° C. (see FIG. 8).

Example 4: In Vitro Release Study

The release of drugs from PCL and PCL-g-PDA films, as obtained in Example 3, was assessed in phosphate buffered saline (PBS, pH 7.4) containing 0.05% v/v Tween 20 at 37° C. under constant orbital shaking (100 rpm). Typically, 10 mg of drug/copolymer film was dived in 20 mL of phosphate buffer solution containing 0.05% of Tween 20 at 37° C. At specific time points, the entire release medium was removed and replaced with 20 mL of fresh buffer solution. The collected sample was analysed by HPLC using UV detection at the maximum absorbance wavelength of the drug (in a range from 200 to 400 nm) using a ratio of acetonitrile/TFA (1000/1) and water/TFA (1000/1) (from 10:90 to 40:60) as mobile phase.

Results:

Drug release kinetics are modified as a function of the presence of PDA in the copolymer, the drug selection and the drug percentage. The PDA content in the copolymer is estimated between 1 wt. % and 20 wt. % by TG analyses. The release kinetics of both dexamethasone and ciprofloxacin hydrochloride are slowed down in PCL-g-PDA films compared to PCL loaded films, and modulated according to the proportion of PDA moieties in the implant. (FIG. 9A and FIG. 9B).

Example 5: Biological (Cytotoxicity) Studies

Fibroblast Cells

The cytotoxicity of PCL-g-PDA film was analysed on L929, mouse fibroblast cell line (NCTC-Clone 929, ECACC 85011425). L929 cells were cultured at 37° C. under humidified 5% CO2 in a DMEM 4.5 g/L D-glucose supplemented with 1 mM L-glutamine, 5% v/v Fetal Bovine Serum, and 100 U per mL penicillin and streptomycin 100 µg per mL. Polyurethane film containing 0.25% zinc dibuthyldithiocarbamate (ZDBC) (Hatano Research Institute, FDSC, batch B-173K) was used as positive reference material (RM) and high density polyethylene film (Hatano Research Institute, FDSC, batch C-161) was used as negative RM. The cells were seeded into 24-well plate a density of 60 000 cell/well and were incubated overnight at 37° C. PCL and PCL-g-PDA films (6 mm of diameter, thickness less than 0.5 mm) were irradiated at 254 nm for 2 minutes twice on each face for decontamination. Films were added into wells and incubated with cells for 24 hours. The films were removed and the medium was replaced by 500 µL of a PrestoBlue® (PB) solution (10% in medium) and incubated for 30 minutes. PB assay was carried out using fluorescence (λex=558 nm, λem=593 nm). Each experiment was performed in triplicate. The PCL-g-PDA copolymers purified in methanol allows cell viability after 24 h of incubation (FIG. 10).

Human Retinal Cells

The cytotoxicity of PCL and PCL-g-PDA film was analysed on ARPE-19 (ATCC, CRL-2302), human retinal epithelial cell line (FIG. 11). ARPE-19 cells were cultured at 37° C. under humidified 5% CO2 in a Dulbecco's Modified Eagle Medium/Nutrient Mixture F-12 (DMEM:F-12, ATCC 30-2006) supplemented with 10% v/v Fetal Bovine Serum. Polyurethane film containing 0.1% zinc diethyldithiocarbamate (ZDEC) (Hatano Research Institute, Food and Drug Safety Center, Japan, batch A-202K) was used as positive reference material (RM) and high density polyethylene film (Hatano Research Institute, Food and Drug Safety Center, Japan, batch C-141) was used as negative RM. The cells were seeded into 24-well plate at a density of 20 000 cells per well and were incubated overnight at 37° C. under humidified 5% CO2. PCL and PCL-g-PDA films and the RM controls (7 mm of diameter, thickness less than 0.5 mm) were irradiated at λ=254 nm for 2 minutes, twice on each face for decontamination. Films were added into wells and incubated with cells for 48 hours. The films were removed and the medium was replaced by a PrestoBlue® (PB) solution (10% in cell culture medium) and incubated for 30 minutes. PB assay was carried out using fluorescence (λex=558 nm, λem=593 nm). Each experiment was performed in quadruplicate.

The percentage of cell viability was calculated using the following formula (1):

$$\%\ \text{cell viability} = \frac{\text{intensity in test well}}{\text{intensity in cell well}} * 100 \quad (1)$$

Example 6: In Vitro Degradation

The kinetics of degradation were studied in vitro on polymer films in standard (PBS at pH=7.4) and accelerated conditions (aqueous solution of HCl (2M) at pH=1) for 75 days at 37° C. Films were cut into implants (dimensions=10×4 mm, thickness=0.3-0.5 mm), weighted (15 mg, $w_{dry,t0}$) and immersed into 0.75 mL of media under stirring according the ISO-10993-13. At predetermined time points, implants were removed from the medium, washed with water, wiped and weighted to determine the wet mass ($w_{we,t}$) then dried under vacuum to constant mass to determine the dry mass ($w_{dry,tx}$). These experiments were carried out in triplicates. The water uptake was calculated from equation (2), the remaining weight from equation (3) and the remaining molecular weight from equation (4). The pH was evaluated using a pH-meter at 20° C.

$$\%\ wateruptake,\ tx = \frac{(w_{wet,tx} - w_{dry,tx})}{w_{dry,tx}} * 100 \quad (2)$$

$$\%\ massresidual,\ tx = \left(1 - \frac{(w_{dry,t0} - w_{dry,tx})}{w_{dry,t0}}\right) * 100 \quad (3)$$

$$\%\ Mnresidual,\ tx = \left(1 - \frac{(M_{n,0} - M_{n,tx})}{M_{n,0}}\right) * 100 \quad (4)$$

Results:

At pH=7.4, PCL-g-PDA implants keeps its initial mass (FIG. 12), molecular weight (FIG. 13) and shape (FIG. 14) without any water-uptake (FIG. 15) and pH remains stable (FIG. 16) during 110 days. At pH=1, PCL-g-PDA implants loose immediately its initial masse (FIG. 17) and molecular weight (FIG. 18), and were broken and brittle (FIG. 19). PCL-g-PDA implants are degradable and are expected to degrade extremely slowly in in vitro in standard conditions without changing in the local pH value.

Example 7: Synthesis of PCL-b-PEG-b-PCL ("T")

In a dry Schlenk flask, PEG (5.0 g, 2.5 mmol, Mn=2 000 g/mol) was solubilized in 55 mL of dry toluene under argon atmosphere. Then, Sn(Oct)2 (0.20 g, 0.5 mmol) and ε-CL monomer (4.99 g, 43.8 mmol, 17.5 eq) were added, still under inert atmosphere. Water and oxygen were removed by three freeze-pump thaw cycles. Reaction was conducted at 100° C. during 24 hours under argon flux and vigorous stirring. Reaction was stopped by adding few drops of HCl solution (0.1 M in methanol). The product was precipitated in cold diethyl ether, filtrated and dried under vacuum.

The molecular weights of triblock copolymers were calculated according to the following equations (5)-(8):

$$DP_{EG} = \frac{M_{n,PEG,th}}{44} \quad (5)$$

$$DP_{CL} = 2 \times DP_{EG} \times \frac{I_{3.99ppm}}{I_{3.50ppm}} \quad (6)$$

$$M_{n,NMR\ PCL} = DP_{CL} \times 114 \quad (7)$$

$$M_{n,NMR,PCL-PEG-PCL} = M_{n,PEG} + M_{n,PCL} \quad (8)$$

With 44 g/mol the molecular weight of an ethylene glycol unit and 114 g/mol the molecular weight of a ε-caprolactone unit.

The conversion is calculated by comparing the DPCL obtained by NMR after purification with the theoretical value. The yield (η) is calculated by comparing the mass of the polymer obtained with the theoretical mass value of polymer obtained taking into account the conversion calculated by NMR.

$$T_{conv} = \frac{DP_{CL,NMR}}{DP_{CL,feed}} * 100 \quad (9)$$

$$m_{th,PCL-PEG-PCL} = m_{PEG} + m_{PCL} \times T_{conv} \quad (10)$$

$$\eta = \frac{m_{PCL-PEG-PCL}}{m_{th,PCL-PEG-PCL}} \times 100 \quad (11)$$

Conversion: 86%

Yield: 93%

$^1$H NMR (600 MHz, DMSOd$_6$): δ=3.99 (t, R—CH2-O—CO), 3.5 (m, R—CH2-O), 2.27 (t, R—CH2-CO—O), 1.54 (m, R—CH2-CH2-CO), 1.30 (m, R—CH2-R)

SEC (THF, RI, PS): Mn=6 143 g/mol, Đ=1.09

SEC (DMF, RI, PEG): Mn=3 529 g/mol, Đ=1.07

Similar to the method described above, the following PCL-b-PEG-b-PCL polymers were synthesized (see Table 4). In Table 4, a polymer of the type PCL-b-PEG-b-PCL, consisting of PEG of 1000 g/mol and PCL of 2000 g/mol will be defined as "1000-2000-1000". Moreover, PCL-b-PEG-b-PCL copolymer will be designated "T" herein.

TABLE 4

Characterizations of T

| Entry | T theoretical | T obtained [a] | CL/EG | $M_n$ [b] (g/mol) | Đ [b] | yield ($\eta_x$) [c] |
|---|---|---|---|---|---|---|
| 1 | 1800-4600-1800 | 1400-4600-1400 | 0.61 | 9 400 | 1.19 | 93 |
| 2 | 1000-4600-1000 | 700-4600-700 | 0.30 | 8 200 | 1.11 | 87 |
| 3 | 2000-2000-2000 | 2100-2000-2100 | 2.13 | 9 300 | 1.14 | 95 |
| 4 | 1200-2000-1200 | 1100-2000-1100 | 1.10 | 6 600 | 1.19 | 94 |
| 5 | 1000-2000-1000 | 855-2000-855 | 0.85 | 6 100 | 1,09 | 92 |
| 6 | 1000-2000-1000 | 890-2000-890 | 0.89 | 6 500 | 1.09 | 95 |

TABLE 4-continued

| Characterizations of T | | | | | | |
|---|---|---|---|---|---|---|
| Entry | T theoretical | T obtained [a] | CL/EG | $M_n$ [b] (g/mol) | Đ [b] | yield ($\eta_x$) [c] |
| 7 | 1000-2000-1000 | 846-2000-846 | 0.49 | 5 570 | 1.18 | 84 |
| 8 | 1100-1400-1100 | 1000-1400-1000 | 1.43 | 5 500 | 1.18 | 77 |
| 9 | 1000-1000-1000 | 940-1000-940 | 1.89 | 4 300 | 1.19 | 77 |

[a] determined by $^1$H NMR in $CDCl_3$ using equation (8);
[b] determined by SEC in THF using PS standards for calibration;
[c] determined using equation (11).

Example 8: Synthesis of Iodinated (PCL-I)-b-PEG-b-(PCL-I) ("T-I")

In a typical experiment, polymers obtained from Example 7, for example PCL-b-PEG-b-PCL of Entry No. 5 in Table 4 (4 g, Mn,NMR=3 710 g/mol, 1.08 mmol, 16.2 mmol of CL units) and anhydrous THF (200 mL) were introduced into a dry conic reactor and put under argon flux until complete dissolution. The solution was then cooled down at −50° C. by diving it into a liquid nitrogen/ethanol mixture before addition of LDA (8.09 mL, 16.2 mmol) under argon. After 30 minutes of reaction, a solution of iodine (4.10 g, 1.62 mmol) in a minimum amount of anhydrous THF was injected with a syringe through a septum and the mixture was kept at −50° C. under stirring and argon atmosphere. After 30 minutes, the reaction was stopped by addition of an aqueous solution of NH4Cl (2 M, 200 mL) and the temperature was increased to 0° C. prior to addition of HCl (aq) (37%) to reach neutral pH. Then, the polymer was extracted from the solution by washing three times with dichloromethane (3×200 mL) in a separating funnel. Organic phases were collected, washed three times with a solution of Na2S2O3 (0.3 M, 3×100 mL), dried using MgSO4 powder, filtrated and concentrated under reduced pressure. The polymer was precipitated in cold diethyl ether, filtrated and dried under vacuum.

Substitution: 23 mol. %

Yield: 50 wt. %

$^1$H NMR (600 MHz, DMSO$d_6$): δ=4.44 (m, R—CHI—CO—O), 3.99 (t, R—CH2-O—CO), 3.50 (m, R—CH2-O), 2.27 (t, R—CH2-CO—O), 1.87 (m, R—CH2-CHI), 1.54 (m, R—CH2-CH2-CO), 1.30 (m, R—CH2-R)

SEC (THF, RI, PS): Mn=5 760 g/mol, Đ=1.28

SEC (DMF, RI, PEG): Mn=3 500 g/mol, Đ=1.24

Example 9: Synthesis of (PCL-g-PDA)-b-PEG-b-(PCL-g-PDA) ("T-PDA")

In a typical experiment, the iodated polymer obtained from Example 8, for example (PCL-I)-b-PEG-b-(PCL-I) (1.5 g, 1.07 mmol of iodinated CL units), is mixed in a first Schlenk flask (Schlenk flask A) with DMSO (20 mL). In a second Schlenk flask (Schlenk flask B), dopamine hydrochloride (5.09 g, 25 eq. with respect to iodinated CL unit, 26.8 mmol), PMDETA (340 μL, 1.5 eq. with respect to iodinated CL unit, 26.8 mmol), $Na_2CO_3$ (300.0 mg), BPO (6.49 g, 25 eq. with respect to iodinated CL unit, 26.8 mmol), and DMSO (37 mL) were added. Solutions were left under stirring and argon flux for 4 hours. Then, oxygen was removed by three freeze-pump thaw cycles. Iodinated PCL solution was transferred to the flask B and copper(I) bromide (0.23 g, 1.5 eq. with respect to iodinated CL, 1.61 mmol) was added. The flask was then dived in an oil bath at 70° C. and vigorous stirring during 48 hours. Reaction was stopped by cooling in a liquid nitrogen bath. Solution was concentrated by evaporating DMSO at 70° C. under vacuum. The polymer was dialyzed in water and freeze-dried.

PDA: 38-49 wt. %

$^1$H NMR (600 MHz, DMSO$d_6$): δ=4.57 (m, R—CH(PDA)—CO), 3.99 (t, R—CH2-O—CO), 3.5 (m, R—CH2-O), 2.27 (t, R—CH2-CO—O), 1.96 (m, R—CH2-CH(PDA)), 1.84 (m, R—CH2-CH(PDA)), 1.54 (m, R—CH2-CH2-CO), 1.30 (m, R—CH2-R)

SEC (DMF, RI, PEG): Mn=3 000 g/mol, Đ=1.24

In the NMR spectrum, the disappearance of the peaks at 4.44 ppm and at 1.87 ppm, which are characteristic signals from the functionalization of PCL by iodine (see Example 8), shows that the chemical environment of the polymer is modified after the introduction and the polymerization of dopamine. Moreover, the appearance of the peaks at 4.57 ppm, 1.96 ppm and 1.84 ppm also confirm this modification of the chemical environment. The corresponding $^1$H-NMR spectrum, i.e. for T-I and T-PDA based on polymer T according to entry No. 5 in Table 4 is shown in FIG. 20. To confirm that the changes of the chemical shifts could be attributed to an effective grafting of PDA side chains onto the PCL backbone, diffusion ordered NMR spectroscopy (DOSY NMR) analyses were performed. Peaks at 4.57 ppm, 1.96 ppm and 1.84 ppm display the same coefficient of diffusion (D=−6.02*10-11 m2. s-1) than the peaks attributed to T, proving the grafting of PDA on the PCL chains (FIG. 21).

The molecular weight of this T-PDA was further analyzed by SEC in DMF, using UV detection at 450 nm. It is important to notice that the previous copolymers were analysed by SEC in THF, but copolymers containing PDA are not soluble in THF.

The PDA content is quantified according to the TGA method as explained in Example 2, using the modified formula:

$$W\ \%_{PDA\ in\ copolymer} = \frac{\%_{remaining\ weight\ in\ T-PDA\ at\ 600°\ C.} - \%_{remaining\ weight\ in\ T\ at\ 600°C.}}{\%_{remaining\ weight\ in\ oligo-PDA\ at\ 600°\ C.}} * 100$$

The proportion of PDA is 38 wt. %. This high value includes the masses of free and grafted PDA in the copolymer which is consistent with the intensities of the peaks detected in NMR (FIG. 20 and FIG. 21). The respective proportion of grafted PDA and free oligo-PDA are unknown.

Example 10: Protein Stability

The stability of mAb was assessed in formulations composed of 5% (w/v) of copolymers (T or T-PDA) in a HBS:$PEG_{400}$1:1 (v/v). The formulation will either contain 40 mg/ml (high dose (HD)) or 13 mg/ml (low dose (LD)) of mAb. In this Example, the formulation will be defined as formulation X-Y, where X is a letter referring to the copolymer (T, T-PDA, T/T-PDA) and Y is a number referring to the mAb dose (LD,HD). The "T" polymer used herein refers to Entry No. 6 of Table 4 in Example 7, and the resulting T-PDA as obtainable with the method described in Example 9. For each formulation, the evolution of the characteristic parameters of SEC is shown in FIG. 22A, FIG. 22B and FIG. 22C. The formulations are details in Table 5.

TABLE 5

Composition of the formulations for the stability and the release of mAb in vitro

| Formulation code | Copolymer | Copolymer (wt. %) | mAb DL (%) |
|---|---|---|---|
| T-LD | T | 5 | 21 |
| T-HD | | | 44 |
| T/T-PDA-LD | T and T-PDA (2:1) | | 22 |
| T/T-PDA-HD | | | 44 |
| T-PDA-LD | T-PDA | | 22 |
| T-PDA-HD | | | 44 |

For the formulation T-HD, the sample solutions were white due to the presence of the white powder of copolymer but turned limpid after the addition of the mobile phase. At day 0 and day 3, the absorbance at 280 nm, the relative wavelength ratio and the relative AUC were nearly constant. Then, from day 3, the intensity and the relative AUC of mAb progressively decreased but the relative wavelength ratio remained constant. These results suggested the interaction of mAb with the copolymer that decreases the amount of mAb detected, which is consistent with the results of the pre-formulations study.

For the formulation T/T-PDA-HD, the sample solutions were black then blurred after the addition of the mobile phase. From day 0 to day 30, the absorbance and the relative AUC of the mAb detected progressively decreased but the relative wavelength ratio remained constant suggesting an interaction of mAb with the copolymer. It should be noted that the absorbance at day 0 of T/T-PDA-HD is divided by 2 compared to formulation of T-HD, showing a stronger initial interaction of mAb towards the mix of T and T-PDA. Besides, the decrease of the amount of mAb detected from day 0 to day 30 is higher in formulation T/T-PDA-HD (93% of mAb detection loss) than in formulation T-HD (63% of mAb detection loss).

For the formulation T-PDA-HD, the absorbance was around 5% at 280 nm but not sufficient at 254 nm to calculate the wavelength ratio at day 0. Then, no mAb was detected from day 3 to day 30. This suggests a strong interaction between mAb and T-PDA. Regarding the pre-formulation stability study, it was shown that a progressive decrease of mAb was observed in the presence of copolymers. These results confirm that the PDA-based copolymers show a strong affinity towards mAb.

As a result, the comparisons of SEC-UV spectra demonstrate that the formulations tested, i.e. 3 formulations composed of HBS:PEG400 (1:1) and 10% (w/v) of copolymer—T, T/T-PDA, and T-PDA—interacted with mAb without denaturation of the mAb. The highest decrease in the amount of mAb was observed in the presence of T-PDA, proving the high affinity of mAb towards PDA.

Example 11: The In-Situ Formation of Depots

The formation and behavior of in-situ depots based on the formulations T-HD, T/T-PDA-HD and T-PDA-HD are shown in FIG. 23A, FIG. 23B and FIG. 23C respectively. The respective LD formulation looked similar. The designations used in the Example (e.g. T-HD) are as established in Example 10.

Immediately after injection (day 0), the formation of in-situ depots at the bottom of the vials can be observed. The formulation T formed gel-like precipitated white chunks at day 3 due to the mechanism of solvent-exchange where PEG400 that diffused into PBS. The aggregates seemed to became smaller from day 5 to day 30. The formulation T/T-PDA formed smaller—due to the lower amount of T—and black—due to the T-PDA—chunks at day 3 and the aspect remained similar until day 30. A slight coloration of the release medium was observed probably due the release of PDA-based impurities (e.g. the ones detected in SEC-UV corresponding to the additional peak). The formulation T-PDA formed a thin film with a part adhering to the bottom at day 3 and the aspect remained similar until today 30. The coloration of the medium induced by the formulations T/T-PDA and T-PDA might be taken into consideration for the administration into the eye. However, it appears that this issue can be solved by introducing further purification steps of the T-PDA polymers used, and does not affect the overall proof of principle demonstrated in this Example.

Preliminary in vitro release of mAb performed in physiological conditions showed the ability of T-PDA to make strong interactions with mAb. It is shown that mAb not bound with the copolymer was released before 3 days in a burst effect, while the bound mAb remained unreleased within 30 days. The T formulation favoured the stability of mAb released while T-PDA based formulations tended to destabilize a fraction of mAb in the release medium at 37° C.

As a conclusion, the present examples demonstrate that T-PDA is offering interesting perspectives in term of injectability for the IVT administration of monoclonal antibodies, or fragments thereof, for example thought a 30G needle, and stability of such antibodies during storage, in particular at 4° C.

The invention claimed is:

1. A pharmaceutical preparation comprising a graft copolymer consisting of poly(ε-caprolactone) and polydopamine (PCL-g-PDA copolymer) and an active pharmaceutical ingredient.

2. The pharmaceutical preparation according to claim 1, wherein the pharmaceutical preparation is an intravitreal implant.

3. The pharmaceutical preparation according to claim 1, wherein the active pharmaceutical ingredient is a small molecule and is present in the pharmaceutical preparation in an amount not less than 10 weight %.

4. The pharmaceutical preparation according to claim 2, wherein the active pharmaceutical ingredient is a small molecule and is present in the intravitreal implant in an amount not less than 10 weight %.

5. The pharmaceutical preparation according to claim 1, wherein the PCL-g-PDA copolymer is a polymer of the type (PCL-g-PDA)-b-PEG-b-(PCL-g-PDA) comprising two PCL-g-PDA chains attached to a PEG chain.

6. The pharmaceutical preparation according to claim 5, wherein the pharmaceutical preparation is an intravitreal implant, and the pharmaceutical preparation forms an in situ gelling depot for sustained release of the active pharmaceutical ingredient upon injection in the eye.

7. The pharmaceutical preparation according to claim 6, wherein the active pharmaceutical ingredient is an antibody.

8. The pharmaceutical preparation according to claim 1, wherein the PCL-g-PDA copolymer comprises poly(ε-caprolactone) of a molecular weight in the range of 1000 g/mol to 200000 g/mol.

9. The pharmaceutical preparation according to claim 1, wherein the PCL-g-PDA copolymer comprises a poly(ε-caprolactone) backbone with a molecular weight of 1000 g/mol to 200000 g/mol and branches of polydopamine with a mass content of 0.1 to 50 weight %.

10. The pharmaceutical preparation according to claim 5, wherein the PEG chain has a molecular weight of up to 20000 g/mol, and the two PCL-g-PDA chains both have the same molecular weight.

11. A pharmaceutical preparation comprising a polymer of formula (II)

(II)

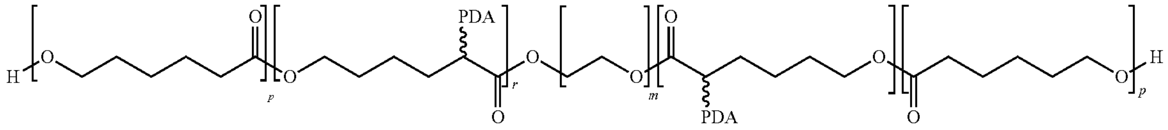

wherein p is 3 to 397, r is 1 to 170, and m is 1 to 170, and an active pharmaceutical ingredient.

12. The pharmaceutical preparation according to claim 11, wherein the pharmaceutical preparation is an intravitreal implant.

13. The pharmaceutical preparation according to claim 12, wherein the pharmaceutical preparation forms an in situ gelling depot for sustained release of an active pharmaceutical ingredient upon injection in the eye.

14. The pharmaceutical preparation according to claim 13, wherein the active pharmaceutical ingredient is an antibody.

15. A method for the treatment of an ocular disease or eye disorder, comprising administering the pharmaceutical preparation according to claim 2.

16. A method for the treatment of an ocular disease or eye disorder, comprising administering the pharmaceutical preparation according to claim 12.

* * * * *